(12) United States Patent
Kubanek et al.

(10) Patent No.: US 8,481,757 B2
(45) Date of Patent: Jul. 9, 2013

(54) COMPOUNDS AND COMPOSITIONS USEFUL IN THE TREATMENT OF MALARIA

(75) Inventors: Julia M. Kubanek, Decatur, GA (US); Mark E. Hay, Atlanta, GA (US); Karine G. Le Roch, Riverside, CA (US); E. Paige Stout, San Diego, CA (US); Amy L. Lane, Jacksonville, FL (US); An-Shen Lin, Taipei (TW)

(73) Assignees: Georgua Tech Research Corporation, Atlanta, GA (US); The Regents of the University of California, Oakland, CA (US)

( * ) Notice: Subject to any disclaimer, the term of this patent is extended or adjusted under 35 U.S.C. 154(b) by 12 days.

(21) Appl. No.: 13/021,171

(22) Filed: Feb. 4, 2011

(65) Prior Publication Data
US 2011/0190338 A1    Aug. 4, 2011

Related U.S. Application Data

(60) Provisional application No. 61/301,354, filed on Feb. 4, 2010.

(51) Int. Cl.
  *A01N 43/02* (2006.01)
(52) U.S. Cl.
  USPC .......................... 549/268; 514/305; 514/450
(58) Field of Classification Search
  USPC .................................. 549/268; 514/305, 450
  See application file for complete search history.

(56) References Cited

U.S. PATENT DOCUMENTS

| | | | |
|---|---|---|---|
| 4,980,360 | A | 12/1990 | Nodiff |
| 5,219,865 | A | 6/1993 | Chatterjee et al. |
| 5,726,166 | A | 3/1998 | Playfair et al. |
| 6,143,756 | A | 11/2000 | Kara et al. |
| 6,528,519 | B1 | 3/2003 | Van Dyke |
| 6,979,740 | B2 | 12/2005 | Jain et al. |
| 2004/0242548 | A1 | 12/2004 | Draper et al. |
| 2005/0159400 | A1 | 7/2005 | Hamann et al. |
| 2007/0032460 | A1 | 2/2007 | Stella et al. |
| 2008/0312287 | A1 | 12/2008 | Hamilton et al. |
| 2011/0015260 | A1 | 1/2011 | Booles et al. |
| 2011/0077258 | A1 | 3/2011 | Carvalho et al. |

OTHER PUBLICATIONS

Lane et al. Journal of Organic Chemistry, 2009, 74, 2736-2742.*
Kubanek et al. Journal of Natural Products, 2006, 69, 731-735.*
Kubanek et al. Organic Letters, 2005, 7, 5261-5264.*
Wolff, Burger's medicinal Chemistry and Drug Discovery, vol. 1, Principles and Practice, John Wiley & sons, New York, 1997.*
Venkatesh et al., J. Pharm. Sci. 89, 145-54 (2000).*
Dorwald F. A. Side Reactions in Organic Synthesis, 2005, Wiley: VCH, Weinheim p. IX of Preface p. 1-15.*
Kubanek et al. Journal of Natural Products (2006), 69(5), 731-735.*
Kubanek J et al. Antineoplastic diterpene-benzoate macrolides from the Fijian red alga *Callophycus serratus*. Organic Letters. 2005; 7(23); 5261-5264.
Kubanek J et al. Bromophycolides C—I from the Fijian red alga *Callophycus serratus*. Journal of Natural Products. 2006; 69(5): 731-735.
Lane Al et al. Callophycoic acids and callophycols from the Fijian red alga *Callophycus serratus*. Journal of Organic Chemistry. 2007; 72(19): 7343-7351.
Esquenazi E et al. Probing marine natural product defenses with DESI-imaging mass spectrometry. PNAS. May 5, 2009; 106(18) 7269-7270.
Lane Al et al. Antimalarial bromophycolides J—Q from the Fijian red alga *Callophycus serratus*. Journal of Organic Chemistry. 2009; 74(7): 2736-2742.
Lane Al et al. Desorption electrospray ionization mass spectrometry reveals surface-mediated antifungal chemical defense of a tropical seaweed. PNAS. May 5, 2009; 106(18): 7314-7319.
Nyadong L et al. Reactive desorption electrospray ionization mass spectrometry (DESI-MS) of natural products of a marine alga. Anal Bioanal Chem. 2009; 394: 245-254.
Cabrita MT et al. Halogenated compounds from marine algae. Marine Drugs. Aug. 9, 2010; 8: 2301-2317.
Lin A-S et al. Bioactive bromophycolides R—U from the Fijian red alga *Callophycus serratus*. Journal of Natural Products. 2010; 73(2): 275-278.
Stout EP et al. Unusual antimalarial meroditerpenes from tropical red macroalgae. Bioorganic & Medicinal Chemistry Letters. 2010; 20: 5662-5665.
Lin H et al. A short asymmetric route to the bromophycolide A and D skeleton. Organic Letters. 2011; 13(5): 1222-1225.
Stout EP et al. Bromophycolide A targets heme crystallization in the human malaria parasite *Plasmodium falciparum*. ChemMedChem. Sep. 6, 2011; 6(9): 1572-1577.

* cited by examiner

*Primary Examiner* — Nizal Chandrakumar
(74) *Attorney, Agent, or Firm* — Myers Bigel Sibley & Sajovec, P.A.

(57) ABSTRACT

Provided herein compounds, compositions and methods useful for the treatment of malaria for a subject in need thereof, including compounds of Formula (I), Formula (II), Formula (III), Formula (IV), and Formula (V).

12 Claims, No Drawings

COMPOUNDS AND COMPOSITIONS USEFUL IN THE TREATMENT OF MALARIA

RELATED APPLICATIONS

This application claims the benefit under 35 U.S.C. §119(e) of U.S. Provisional Patent Application Ser. No. 61/301,354, filed Feb. 4, 2010, the disclosure of which is incorporated herein by reference in its entirety.

STATEMENT OF GOVERNMENT SUPPORT

This invention was made with Government support under Agreement/Contract Numbers 1 U01 TW007401 and 1 R21 TW006662, awarded by the National Institutes of Health. The Government has certain rights in the invention.

FIELD

The present invention concerns the treatment of subjects afflicted with or at risk for development of malaria.

BACKGROUND

Malaria is a major human health concern in many tropical and sub-tropical regions, and current antimalarial drugs are becoming increasingly ineffective due to emerging and spreading resistance. *Plasmodium falciparum*, the most deadly human malaria parasite, poses a major threat to human health worldwide, with over 500 million clinical cases and 1-3 million deaths annually. Snow et al., "The global distribution of clinical episodes of *Plasmodium falciparum* malaria," *Nature* 434:241-217 (2005).

Natural products and their synthetic derivatives have provided the greatest number of successful antimalarial treatments to date, representing approximately 65% of prescribed drugs. Newman et al., "Natural products as sources of new drugs over the last 25 years," *J Nat Prod* 70:461-477 (2007). Quinine, discovered from cinchona tree bark, has been used to treat malaria since the 17th century and was the primary antimalarial drug until it was replaced by chloroquine, a synthetic derivative, in the 1940s. Hyde, "Drug-resistant malaria," *Trends Parasitol* 21:494-498 (2005). Chloroquine became the mainstay antimalarial agent until resistant strains began to appear over a decade after its introduction. Artemisinin, isolated from the plant *Artemisia annua* used in traditional Chinese medicine, ushered in a new wave of antimalarials and became the most potent and rapid-acting drug available. Klayman, "Qinghaosu (artemisinin)—an antimalarial drug from China," *Science* 228:1049-1055 (1985). Several artemisinin synthetic derivatives have since been developed, and artemisinin-based combination therapies are currently being used throughout the world to treat this parasitic disease. However, artemisinin-resistant strains have recently been reported (Dondorp et al., "Artemisinin resistance in *Plasmodium falciparum* malaria," *N Engl J Med* 361:455-467 (2009)), and new antiparasitic drugs are urgently needed to combat these strains.

SUMMARY

Provided herein are compounds and compositions useful for treating malaria. For example, provided is a compound of Formula (IV):

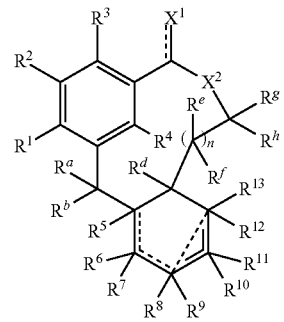

(IV)

wherein:

n=2 to 10, saturated or unsaturated;

$R^1$, $R^2$, $R^3$ and $R^4$ are each independently selected from the group consisting of: H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate;

$R^a$, $R^b$ and $R^d$ are each independently selected from the group consisting of: H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate;

$R^5$, $R^6$, $R^7$, $R^8$, $R^9$, $R^{10}$, $R^{11}$, $R^{12}$ and $R^{13}$, when present (depending on saturation), are each independently selected from the group consisting of: H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate;

Each occurrence of $R^e$ and $R^f$, when present (depending on saturation), is independently selected from the group consisting of: H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate; or one or more pairs of $R^e$ or $R^f$, when present, may together form a ring;

$R^g$ and $R^h$ are each independently selected from the group consisting of: H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester ether, sulfate or phosphate; or $R^g$ and $R^h$ may together form a ring;

$X^1$ and $X^2$ are each independently O or NR', wherein R' is selected from the group consisting of: H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate;

or a pharmaceutically acceptable salt or prodrug thereof.

This formula may be unsubstituted or substituted (e.g., 1, 2, 3, or 4 times) with a suitable substituent such as halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate.

In some embodiments, the compound is a compound of Formula (IV)(A):

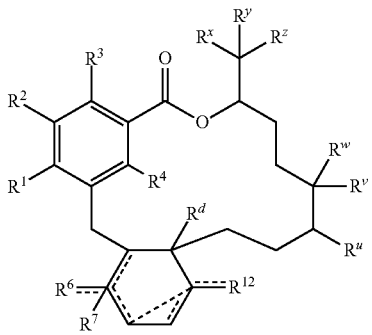

(IV)(A)

wherein:

R¹ is selected from the group consisting of H, halo, hydroxy, alkoxy, carboxy and ester;

R², R³ and R⁴ are each independently selected from the group consisting of: H, halo, alkyl, alkenyl, and alkynyl;

R⁶, R¹² and $R^d$ are each independently selected from the group consisting of: H, halo, alkyl, alkenyl, and alkynyl;

$R^u$, $R^w$ and $R^v$ are each independently selected from the group consisting of: H, halo, hydroxy, alkyl, alkenyl, alkynyl, carbonyl, carboxy, and ester; or ($R^w$ and $R^v$) and $R^u$ may together form an epoxide group;

$R^x$, $R^y$ and $R^z$ are each independently selected from the group consisting of: H, halo, hydroxy, alkyoxy, alkyl, alkenyl, alkynyl, carboxy, and ester;

or a pharmaceutically acceptable salt or prodrug thereof.

This formula may be unsubstituted or substituted (e.g., 1, 2, 3, or 4 times) with a suitable substituent such as halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate.

In some embodiments, the compound is a compound of Formula (IV)(A)(i):

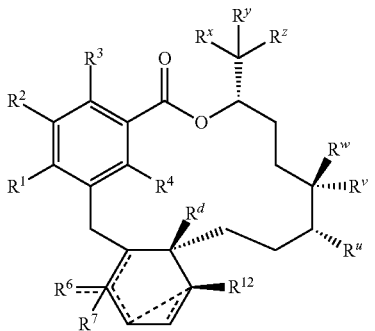

(IV)(A)(i)

wherein:

R¹ is selected from the group consisting of; H, halo, hydroxy, alkyl, alkenyl, alkynyl, alkoxy, carbonyl, carboxy, and ester;

R², R³ and R⁴ are each independently selected from the group consisting of: H, halo, alkyl, alkenyl, and alkynyl;

R⁶, R¹² and $R^d$ are each independently selected from the group consisting of: H, halo, alkyl, alkenyl, and alkynyl;

$R^u$, $R^w$ and $R^v$ are each independently selected from the group consisting of: H, halo, hydroxy, alkyl, alkenyl, alkynyl, carbonyl, carboxy, and ester; or ($R^w$ or $R^v$) and $R^u$ may together faun an epoxide group;

$R^x$, $R^y$ and $R^z$ are each independently selected from the group consisting of: H, halo, hydroxy, alkoxy, alkyl, alkenyl, alkynyl, carboxy, and ester;

or a pharmaceutically acceptable salt or prodrug thereof.

This formula may be unsubstituted or substituted (e.g., 1, 2, 3, or 4 times) with a suitable substituent such as halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate.

In some embodiments, the compound is a compound of Formula (IV)(B):

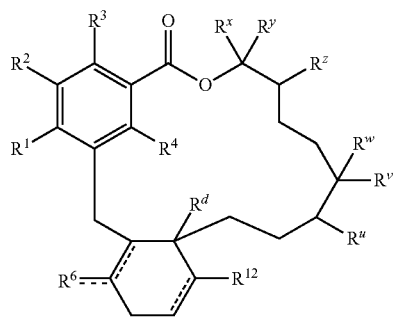

(IV)(B)

wherein:

R¹ is selected from the group consisting of H, halo, hydroxy, carboxy and ester;

R², R³ and R⁴ are each independently selected from the group consisting of: H, halo, alkyl, alkenyl, and alkynyl;

R⁶, R¹² and $R^d$ are each independently selected from the group consisting of: H, halo, alkyl, alkenyl, and alkynyl;

$R^u$, $R^w$ and $R^v$ are each independently selected from the group consisting of: H, halo, hydroxy, alkyl, alkenyl, alkynyl, carbonyl, carboxy, and ester; or ($R^w$ or $R^v$) and $R^u$ may together form ring (e.g., together forming an epoxide group);

$R^x$, $R^y$ and $R^z$ are each independently selected from the group consisting of: H, halo, hydroxy, alkyl, alkenyl, alkynyl, carboxy, and ester;

or a pharmaceutically acceptable salt or prodrug thereof.

This formula may be unsubstituted or substituted (e.g., 1, 2, 3, or 4 times) with a suitable substituent such as halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate.

In some embodiments, the compound is a compound of Formula (IV)(B)(i):

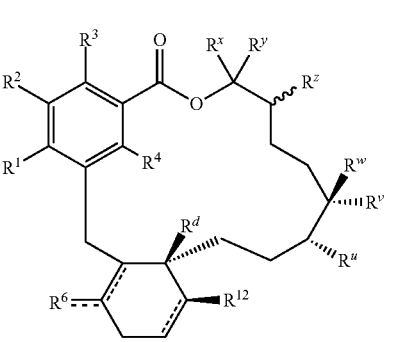

(IV)(B)(i)

wherein:

R¹ is selected from the group consisting of H, halo, hydroxy, carboxy and ester;

$R^2$, $R^3$ and $R^4$ are each independently selected from the group consisting of: H, halo, alkyl, alkenyl, and alkynyl;

$R^6$, $R^{12}$ and $R^d$ are each independently selected from the group consisting of: H, halo, alkyl, alkenyl, and alkynyl;

$R^u$, $R^w$ and $R^v$ are each independently selected from the group consisting of: H, halo, hydroxy, alkyl, alkenyl, alkynyl, carbonyl, carboxy, and ester; or ($R^w$ or $R^v$) and $R^u$ may together form ring (e.g., together forming an epoxide group);

$R^x$, $R^y$ and $R^z$ are each independently selected from the group consisting of: H, halo, hydroxy, alkyl, alkenyl, alkynyl, carboxy, and ester;

or a pharmaceutically acceptable salt or prodrug thereof.

This formula may be unsubstituted or substituted (e.g., 1, 2, 3, or 4 times) with a suitable substituent such as halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate.

Also provided are compounds and compositions comprising a compound of Formula (V):

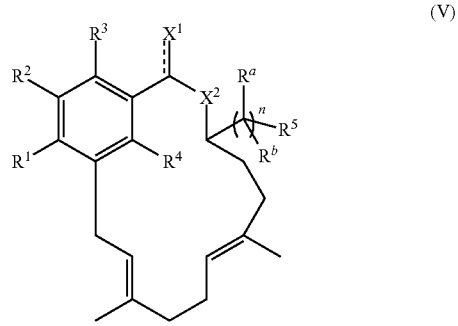

(V)

wherein:

n=1–10, saturated or unsaturated;

$R^1$, $R^2$, $R^3$, $R^4$ and $R^5$ are each independently selected from the group consisting of: H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate;

$R^a$ and $R^b$ when present (depending on saturation), are each independently selected from the group consisting of: H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate;

$X^1$ and $X^2$ are each independently O or NR', wherein R' is selected from the group consisting of: H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate;

or a pharmaceutically acceptable salt or prodrug thereof.

This formula may be unsubstituted or substituted (e.g., 1, 2, 3, or 4 times) with a suitable substituent such as halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate.

In some embodiments of Formula (V):

$R^1$ is selected from the group consisting of: H, halo, hydroxy, alkyl, alkenyl, alkynyl, alkoxy, carbonyl, and carboxy;

$R^2$, $R^3$, $R^4$ and $R^5$ are each independently selected from the group consisting of: H, halo, alkyl, alkenyl, and alkynyl;

$R^a$ and $R^b$ when present (depending on saturation), are each independently selected from the group consisting of: H, halo, hydroxy, alkoxy, alkyl, alkenyl, carbonyl, carboxy, ester, ether, sulfate or phosphate; and $X^1$ and $X^2$ are each independently O;

or a pharmaceutically acceptable salt or prodrug thereof.

This formula may be unsubstituted or substituted (e.g., 1, 2, 3, or 4 times) with a suitable substituent such as halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate.

In some embodiments, the composition is formulated for oral, rectal, or parenteral administration.

In some embodiments, the composition further comprises another anti-malaria agent, e.g., quinine, chlorquinine, artemisinin, and an artemisinin derivative (e.g., artesunate, artemether, dihydroartemisinin, artelinic acid, arteminol, artemotil, arterolane, etc.).

Methods of treating malaria in a subject in need thereof comprising administering a compound or composition as described here to said subject in a treatment effective amount are also provided. In some embodiments, another anti-malaria agent may be administered in combination therewith.

DETAILED DESCRIPTION OF THE EMBODIMENTS

Provided herein and further described below are compounds, compositions and methods useful for the treatment of malaria in a subject in need thereof.

The disclosures of all United States patent references cited herein are hereby incorporated by reference to the extent they are consistent with the disclosure set forth herein. As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" or "/" refers to and encompasses any and all possible combinations of one or more of the associated listed items, as well as the lack of combinations when interpreted in the alternative ("or").

"Malaria" is a mosquito-borne disease caused by the infection of a eukaryotic protist of the genus *Plasmodium*. After a period of typically between two weeks and several months (and occasionally years) spent in the liver, the malaria parasites start to multiply within red blood cells, causing symptoms that include fever and headache. In severe cases, the disease worsens, and may lead to hallucinations, coma, and even death.

As used herein, the term "treating malaria" is intended to generally include combating the infection or possible infection by a protist of the genus *Plasmodium*, whether or not the subject has experienced symptoms caused by the multiplication of this protist in the host, such as fever and headache, and whether or not a *Plasmodium* infection has, in fact, been confirmed. As known in the art, an "infection" is the colonization of a subject by parasitic species. Infecting parasites seek to use the host's resources to reproduce, often, but not always, resulting in disease.

"Treating" refers to any type of treatment that imparts a benefit to a subject, e.g., a subject afflicted with a disease (e.g., malaria) and/or infected with an organism that causes disease (e.g., a malaria-causing parasite such as *Plasmodium falciparum*). Treating includes actions taken and actions refrained from being taken for the purpose of improving the condition of the subject (e.g., the relief of one or more symptoms), delay in the onset or progression of the disease, lessening of one or more symptoms associated with the disease, etc. Treating as used herein also refers to prophylactic or cautionary treatment of a subject at risk for developing a disease, e.g., a subject at risk for being infected with a malaria-causing parasite (e.g., by the subject traveling to a location known for malaria risk).

"Subjects" are, in general, human subjects, but may also include other animal subjects (e.g., laboratory animals), particularly mammalian subjects such as dogs, cats, rabbits, horses, cattle, sheep, etc. for veterinary purposes. Subjects may be of any age, including infantile, juvenile, adolescent, teenage, young adult, adult, middle-age, elderly and geriatric subjects. Human subjects may also be of any ethnicity, e.g., Caucasian, African-American, Hispanic, Asian, Indian, etc.

At least five species of the *Plasmodium* parasite are known to infect humans and cause malaria: *Plasmodium falciparum*, *Plasmodium vivax*, *Plasmodium ovale*, *Plasmodium malariae* and *Plasmodium knowlesi*. The most serious forms of malaria are typically caused by *Plasmodium falciparum*. Malaria caused by *Plasmodium vivax, Plasmodium ovale* and *Plasmodium malariae* usually result in a relatively milder disease in humans. *Plasmodium knowlesi* causes malaria in macaques, but can also infect humans.

Symptoms of malaria may include fever, shivering, arthralgia (joint pain), vomiting, anemia (caused by hemolysis), hemoglobinuria, retinal damage, and/or convulsions. A classic symptom of malaria is the cyclical occurrence of sudden coldness, followed by rigor, and then fever and sweating lasting four to six hours. This may occur approximately every two days in *P. vivax* and *P. ovale* infections, and every three days for *P. malariae. P. falciparum* can present with a recurrent fever every 36-48 hours, or a less pronounced and almost continuous fever. Abnormal posturing indicative of brain damage may also be seen, particularly in children.

Severe malaria (usually seen with a *P. falciparum* infection) normally appears approximately 6-14 days after infection. Symptoms of severe malaria may include splenomegaly (enlarged spleen), severe headache, cerebral ischemia, hepatomegaly (enlarged liver), hypoglycemia, and hemoglobinuria with renal failure.

Chronic malaria, where the disease can relapse months or years after exposure, due to the presence of latent parasites in the liver, is seen in both *P. vivax* and *P. ovale* (but usually not in *P. falciparum*). Describing a case of malaria as cured by observing the disappearance of parasites from the bloodstream can, therefore, be deceptive, and thus, in some embodiments administration of active agents to a subject at risk for malaria may be warranted whether or not an infection can be detected.

I. Active Agents

Active agents useful in the methods of treating malaria as described herein are provided below. Active agents as described herein can be isolated and/or prepared as detailed herein or in accordance with known procedures or variations thereof that will be apparent to those skilled in the relevant art.

Active agents may be used or administered alone or in combination with one or more other anti-malarial agents, such as quinine, chlorquine, artemisinin or an artemisinin derivative (e.g., artesunate, artemether, dihydroartemisinin, artelinic acid, arteminol, artemotil, arterolane, etc.) The administration of two or more compounds "in combination" or "in conjunction" means that the two compounds are administered closely enough in time to have an additive and/or synergistic effect. The two compounds may be administered simultaneously (concurrently) or sequentially. Simultaneous administration may be carried out by mixing the compounds prior to administration, or by administering the compounds at the same point in time but at different anatomic sites or using different routes of administration.

The active agents of the various formulas disclosed herein may contain chiral centers, e.g. asymmetric carbon atoms. Thus, the present invention is concerned with both: (i) racemic mixtures of the active agents, and (ii) enantiomeric forms of the active agents. The resolution of racemates into enantiomeric forms can be done in accordance with known procedures in the art. For example, the racemate may be converted with an optically active reagent into a diastereomeric pair, and the diastereomeric pair subsequently separated into the enantiomeric forms.

Geometric isomers of double bonds and the like may also be present in the compounds disclosed herein, and all such stable isomers are included within the present invention unless otherwise specified. Also included are tautomers and rotamers.

"H" refers to a hydrogen atom. "C" refers to a carbon atom. "N" refers to a nitrogen atom. "O" refers to an oxygen atom. "Halo" refers to fluoro, chloro, bromo or iodo. The term "hydroxy," as used herein, refers to an —OH moiety.

An "acyl" is intended to mean a group —C(O)—R, where R is a suitable substituent (for example, an acetyl group, a propionyl group, a butyroyl group, a benzoyl group, or an alkylbenzoyl group).

"Alkyl," as used herein, refers to a straight or branched chain hydrocarbon containing from 1 or 2 to 10 or 20 or more carbon atoms (e.g., C2, C3, C4, C5, C6, C7, C8, C9, C10, C11, C12, C13, C14, C15, etc.). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. The alkyl may be optionally substituted with from 1 to 4 suitable substituents, as chemically feasible.

The term "optionally substituted" indicates that the specified group is either unsubstituted, or substituted by one or more suitable substituents. A "substituent" is an atom or atoms substituted in place of a hydrogen atom on the parent chain or cycle of an organic molecule, for example, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate.

Dotted bond lines used in the formulas presented herein indicate possible additional bonds.

As generally understood by those of ordinary skill in the art, "saturation" refers to the state in which all available valence bonds of an atom (e.g., carbon) are attached to other atoms. Similarly, "unsaturation" refers to the state in which not all the available valence bonds are attached to other atoms; in such compounds the extra bonds usually take the form of double or triple bonds (usually with carbon). For example, a carbon chain is "saturated" when there are no double or triple bonds present along the chain or directly connected to the chain (e.g., a carbonyl), and is "unsaturated" when at least one double or triple bond is present along the chain or directly connected to the chain (e.g., a carbonyl). Further, the presence or absence of a substituent depending upon chain saturation will be understood by those of ordinary skill in the art to depend upon the valence requirement of the atom or atoms to which the substituent binds (e.g., carbon).

"Alkenyl," as used herein, refers to a straight or branched chain hydrocarbon containing from 1 or 2 to 10 or 20 or more carbons, and containing at least one carbon-carbon double bond, formed structurally, for example, by the replacement of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like. This group may be optionally substituted with from 1 to 4 suitable substituents, as chemically feasible.

"Alkynyl," as used herein, refers to a straight or branched chain hydrocarbon group containing from 1 or 2 to 10 or 20 or more carbon atoms, and containing at least one carbon-carbon triple bond. Representative examples of alkynyl include, but are not limited, to acetylenyl, 1-propynyl, 2-propynyl, 3-butynyl, 2-pentynyl, 1-butynyl and the like. This group may be optionally substituted with from 1 to 4 suitable substituents, as chemically feasible.

The term "cycloalkyl," as used herein, refers to a saturated cyclic hydrocarbon group containing from 3 to 8 carbons or more. Representative examples of cycloalkyl include, cyclopropyl, cyclobutyl, cyclopentyl, cyclohexyl, cycloheptyl, and cyclooctyl. This group may be optionally substituted with from 1 to 4 suitable substituents, as chemically feasible.

"Heterocyclo," as used herein, refers to a monocyclic or a bicyclic ring system. Monocyclic heterocycle ring systems are exemplified by any 5 or 6 member ring containing 1, 2, 3, or 4 heteroatoms independently selected from the group consisting of: O, N, and S. The 5 member ring has from 0 to 2 double bonds, and the 6 member ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, sulfoxide, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like. This group may be optionally substituted with from 1 to 4 suitable substituents, as chemically feasible.

"Aryl" as used herein refers to a fused ring system having one or more aromatic rings. Representative examples of aryl include, azulenyl, indanyl, indenyl, naphthyl, phenyl, tetrahydronaphthyl, and the like. The aryl groups of this invention can be substituted with 1, 2, 3, 4, or 5 substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, aryloxy, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, —NR'R" (wherein, R' and R" are independently selected from hydrogen, alkyl, alkylcarbonyl, aryl, arylalkyl and formyl), and —C(O)NR'R" (wherein R' and R" are independently selected from hydrogen, alkyl, alkylcarbonyl, aryl, arylalkyl, and formyl). This group may be optionally substituted with from 1 to 4 suitable substituents, as chemically feasible.

"Heteroaryl" means a cyclic, aromatic hydrocarbon in which one or more carbon atoms have been replaced with heteroatoms. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from the group consisting of: O, N, and S. The heteroaryl group, including each heteroatom, can be unsubstituted or substituted with from 1 to 4 suitable substituents, as chemically feasible. For example, the heteroatom S may be substituted with one or two oxo groups, which may be shown as =O.

"Alkoxy," as used herein, refers to an alkyl group, as defined herein, appended to the parent molecular moiety through an oxy group, as defined herein. Representative examples of alkoxy include, but are not limited to, methoxy, ethoxy, propoxy, 2-propoxy, butoxy, tert-butoxy, pentyloxy, hexyloxy and the like.

An "amino" refers to a primary (—NH$_2$), secondary (—NRH) or tertiary amine (—NR$_2$), wherein R is a suitable substituent as described herein, such as alkyl, alkenyl, alkynyl, cycloalkyl, heterocyclo, aryl, heteroaryl, alkoxy, carbonyl, carboxy, etc. Tertiary amines may have substituents that are bridging, i.e., form a heterocyclic ring structure that includes the amine nitrogen.

"Nitro" refers to the organic compound functional group –NO$_2$.

An "amide" as used herein refers to an organic functional group having a carbonyl group (C=O) linked to a nitrogen atom (N), or a compound that contains this group, generally depicted as:

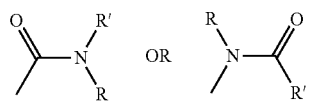

wherein, R and R' can independently be any suitable substituent, such as alkyl, alkenyl, alkynyl, cycloalkyl, heterocyclo, aryl, heteroaryl, alkoxy, carbonyl, carboxy, etc.

A "phosphate" refers to the functional group:

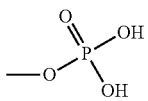

A "sulfate" refers to the functional group:

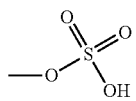

A "sulfone" as used herein refers to a sulfonyl functional group, generally depicted as:

wherein, R can be any suitable substituent, such as alkyl, alkenyl, alkynyl, cycloalkyl, heterocyclo, aryl, heteroaryl, alkoxy, carbonyl, carboxy, etc.

A "sulfoxide" as used herein refers to a sulfinyl functional group, generally depicted as:

wherein, R can be any suitable substituent, such as alkyl, alkenyl, alkynyl, cycloalkyl, heterocyclo, aryl, heteroaryl, alkoxy, carbonyl, carboxy, etc.

A "thiol" or "mercapto" refers to an —SH group or to its tautomer =S.

The term "oxo," as used herein, refers to a =O moiety. The term "oxy," as used herein, refers to a —O— moiety.

"Carbonyl" is a functional group having a carbon atom double-bonded to an oxygen atom (—C=O).

"Carboxy" as used herein refers to a —COOH functional group, also written as —(C=O)—OH.

"Ester" as used herein refers to a group —COOR (or —(C=O)—OR), wherein R is a suitable substituent, for example, alkyl, alkenyl or alkynyl.

"Ether" refers to a group —R—O—R'—, wherein R and R' are each independently a suitable substituent, for example, alkyl, akenyl, alkyneyl, cycloalkyl, aryl, etc.

"Form a ring" as used herein, with respect to two substituents together forming a ring, refers to the two groups together forming an alkylidene chain. Rings may be aromatic or aliphatic. "Alkylidene chain" as used herein refers to a difunctional organic group which can be linear, branched, and/or cyclic or polycyclic (e.g., containing 2 or 3 to 8, 12 or 16 carbon atoms), which difunctional organic group may be substituted or unsubstituted, and which may be saturated or unsaturated, and which one or more of each of the carbons may optionally substitued for a heteroatom selected from the group consisting of N, O, and S. Examples include but are not limited to alkylene, alkenylene, alkynylene, arylene, alkarylene, and aralkylene. See, e.g., U.S. Pat. No. 6,946,533.

"Pharmaceutically acceptable" as used herein means that the compound or composition is suitable for administration to a subject to achieve the treatments described herein, without unduly deleterious side effects in light of the severity of the disease and necessity of the treatment.

A "pharmaceutically acceptable salt" is intended to mean a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

A "prodrug" is intended to mean a compound that is converted under physiological conditions or by solvolysis or metabolically to a specified compound that is pharmaceutically active. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein in their entirety.

Provided herein are compounds of Formula (I), Formula (II), and Formula (III):

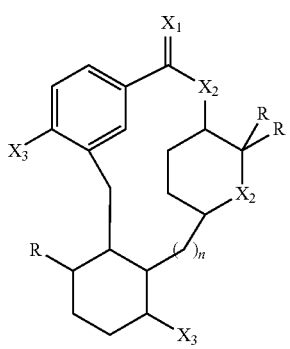

(I)

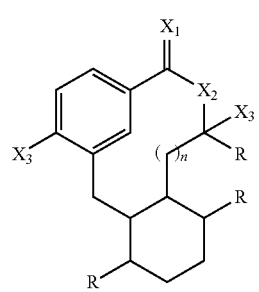

(II)

-continued

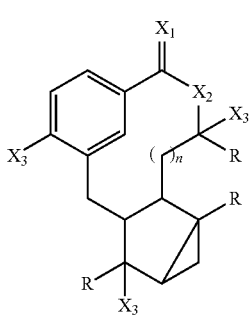
(III)

wherein:
n=1-10;
$X_1$=O, NR, or $CR_2$;
$X_2$=O or NR; and
$X_3$=OR, $NR_2$, or halo;
wherein R=H, alkyl, alkenyl or alkynyl;
or a pharmaceutically acceptable salt or prodrug thereof.

These formulas may be unsubstituted or substituted (e.g., 1, 2, 3, or 4 times) with a suitable substituent such as halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, and ester, and unsaturations can be placed throughout the macrocycle and six-membered rings.

Further provided are compounds of Formula (IV):

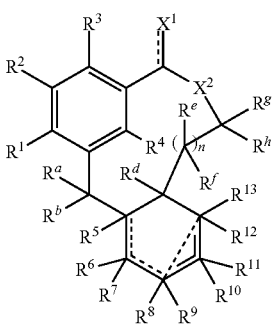
(IV)

wherein:
n=1 or 2 to 10, saturated or unsaturated;
$R^1$, $R^2$, $R^3$ and $R^4$ are each independently selected from the group consisting of: H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate;

$R^a$, $R^b$ and $R^d$ are each independently selected from the group consisting of: H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate;

$R^5$, $R^6$, $R^7$, $R^8$, $R^9$, $R^{10}$, $R^{11}$, $R^{12}$ and $R^{13}$, when present (depending on saturation), are each independently selected from the group consisting of: H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate;

Each occurrence of $R^e$ and $R^f$, when present (depending on saturation), is independently selected from the group consisting of: H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate; or one or more pairs of $R^e$ or $R^f$, when present, may together form a ring;

$R^g$ and $R^h$ are each independently selected from the group consisting of: H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate and phosphate; or $R^g$ and $R^h$ may together form a ring;

$X^1$ and $X^2$ are each independently O or NR', wherein R' is selected from the group consisting of: H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate and phosphate;

or a pharmaceutically acceptable salt or prodrug thereof.

This formula may be unsubstituted or substituted (e.g., 1, 2, 3, or 4 times) with a suitable substituent such as halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate.

Examples of Formula (IV) include Formula (IV)(A) and Formula (IV)(A)(i):

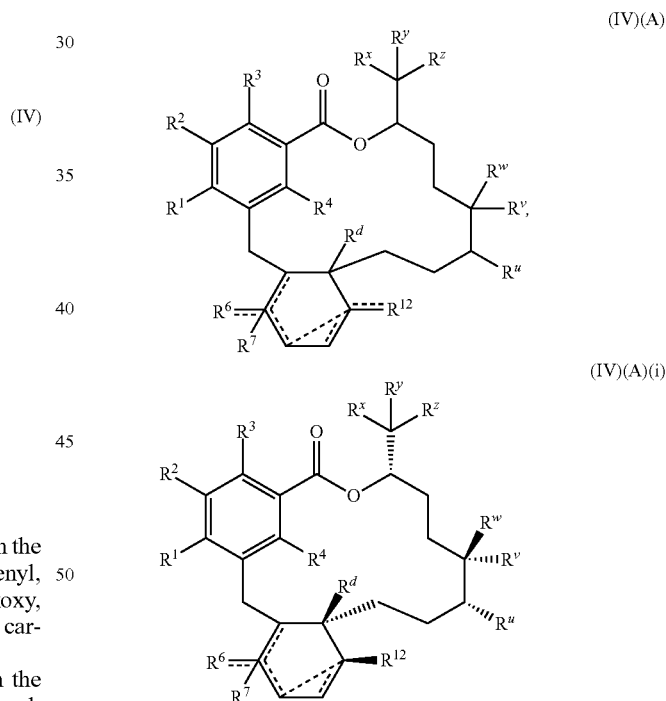

wherein:
$R^1$ is selected from the group consisting of H, halo, hydroxy, carboxy and ester;
$R^2$, $R^3$ and $R^4$ are each independently selected from the group consisting of: H, halo, alkyl, alkenyl, and alkynyl;
$R^6$, $R^{12}$ and $R^d$ are each independently selected from the group consisting of: H, halo, alkyl, alkenyl, and alkynyl;
$R^u$, $R^w$ and $R^v$ are each independently selected from the group consisting of: H, halo, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate and phosphate; or ($R^w$ or $R^v$) and $R^u$ may together form ring (e.g., together forming an epoxide group);

$R^x$, $R^y$ and $R^z$ are each independently selected from the group consisting of: H, halo, hydroxy, alkyl, alkenyl, alkynyl, carboxy, ester, ether, sulfate and phosphate;

or a pharmaceutically acceptable salt or prodrug thereof.

This formula may be unsubstituted or substituted (e.g., 1, 2, 3, or 4 times) with a suitable substituent such as halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate.

Examples of Formula (IV) also include Formula (IV)(B) and Formula (IV)(B)(i):

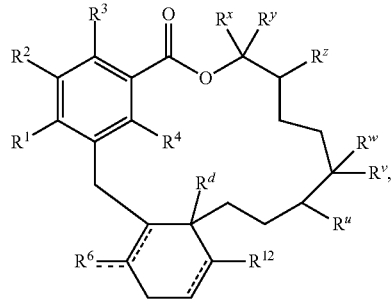

(IV)(B)

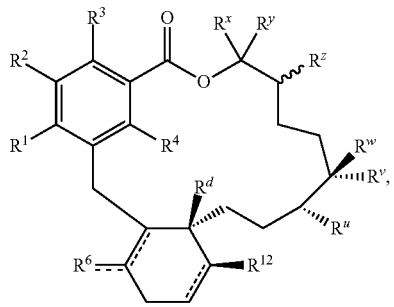

(IV)(B)(i)

wherein:

$R^1$ is selected from the group consisting of H, halo, hydroxy, carboxy and ester;

$R^2$, $R^3$ and $R^4$ are each independently selected from the group consisting of: H, halo, alkyl, alkenyl, and alkynyl;

$R^6$, $R^{12}$ and $R^d$ are each independently selected from the group consisting of: H, halo, alkyl, alkenyl, and alkynyl;

$R^u$, $R^w$ and $R^v$ are each independently selected from the group consisting of: H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate and phosphate; or ($R^w$ or $R^v$) and $R^u$ may together form ring (e.g., together forming an epoxide group);

$R^x$, $R^y$ and $R^u$ are each independently selected from the group consisting of: H, halo, hydroxy, alkyl, alkenyl, alkynyl, carboxy, ester, ether, sulfate and phosphate;

or a pharmaceutically acceptable salt or prodrug thereof.

This formula may be unsubstituted or substituted (e.g., 1, 2, 3, or 4 times) with a suitable substituent such as halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate.

Also provided are compounds of Formula (V):

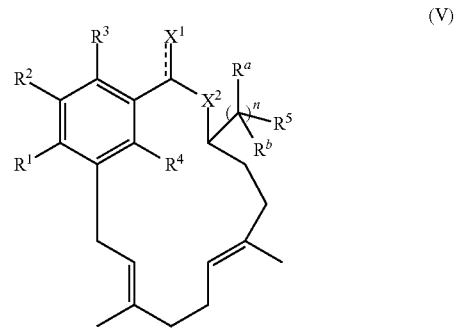

(V)

wherein:

n=1-10, saturated or unsaturated;

$R^1$, $R^2$, $R^3$, $R^4$ and $R^5$ are each independently selected from the group consisting of: H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate and phosphate;

$R^a$ and $R^b$ when present (depending on saturation), are each independently selected from the group consisting of: H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate and phosphate;

$X^1$ and $X^2$ are each independently O or NR', wherein R' is selected from the group consisting of: H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate and phosphate;

or a pharmaceutically acceptable salt or prodrug thereof.

This formula may be unsubstituted or substituted (e.g., 1, 2, 3, or 4 times) with a suitable substituent such as halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, ester, ether, sulfate or phosphate.

II. Compositions

In some embodiments, compositions comprising a carrier and an effective amount of active agent are provided. An "effective amount" of an active agent is that amount needed to carry out the composition's function of treatment of malaria.

In some embodiments, the carrier is a pharmaceutically acceptable carrier. A "pharmaceutically acceptable carrier" as used herein refers to a carrier that, when combined with an active agent of the present invention, facilitates the application or administration of that active agent for its intended purpose (e.g., as a treatment for malaria).

The active agents may be formulated for administration in a pharmaceutically acceptable carrier in accordance with known techniques. See, e.g., Remington, *The Science And Practice of Pharmacy* (9$^{th}$ Ed. 1995). The pharmaceutically acceptable carrier must, of course, also be acceptable in the sense of being compatible with any other ingredients in the composition. The carrier may be a solid or a liquid, or both, and is preferably formulated with the compound as a unit-dose composition, for example, a tablet, which may contain from 0.01 or 0.5% to 95% or 99% by weight of the active compound. One or more active compounds may be included in the compositions of the invention, which may be prepared by any of the well-known techniques of pharmacy comprising admixing the components, optionally including one or more accessory ingredients.

In general, compositions may be prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

The compositions of the invention include those suitable for oral, rectal, topical, buccal (e.g., sub-lingual), vaginal, parenteral (e.g., subcutaneous, intramuscular, intradermal, or intravenous), and transdermal administration, although the most suitable route in any given case will depend on the nature and severity of the condition being treated and on the nature of the particular active compound that is being used.

Compositions suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such compositions may be prepared by any suitable method of pharmacy, which includes the step of bringing into association the active compound and a suitable carrier (which may contain one or more accessory ingredients as noted above).

Compositions suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Compositions suitable for parenteral administration comprise sterile aqueous and non-aqueous injection solutions of the active compound. These preparations may contain antioxidants, buffers, bacteriostats and solutes that render the composition isotonic with the blood of the intended recipient. Aqueous and non-aqueous sterile suspensions may include suspending agents and thickening agents. The compositions may be presented in unit/dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

Compositions suitable for rectal administration are preferably presented as unit dose suppositories. These may be prepared by mixing the active compound with one or more conventional solid carriers, for example, cocoa butter, and then shaping the resulting mixture.

For example, in one aspect, there is provided an injectable, stable, sterile composition comprising, a compound of any or Formulas (I)-(VI), or a salt or prodrug thereof, in a unit dosage form in a sealed container. The compound or salt is provided in the form of a lyophilizate that is capable of being reconstituted with a suitable pharmaceutically acceptable carrier to form a liquid composition suitable for injection thereof into a subject. When the compound or salt is substantially water-insoluble, a sufficient amount of emulsifying agent that is physiologically acceptable may be employed in sufficient quantity to emulsify the compound or salt in an aqueous carrier.

The present invention is explained in greater detail in the following non-limiting examples.

EXAMPLE 1

Bromophycolides A-Q and Biological Activities

Bromophycolides J-Q (1-8) were isolated from extracts of the Fijian red alga *Callophycus serratus* and identified with 1D and 2D NMR spectroscopy and mass spectral analyses. These diterpene-benzoate macrolides represent two novel carbon skeletons and add to the ten previously reported bromophycolides (9-18) from this alga. Among these 18 bromophycolides, several exhibited activities in the low micromolar range against the human malaria parasite *Plasmodium falciparum*.

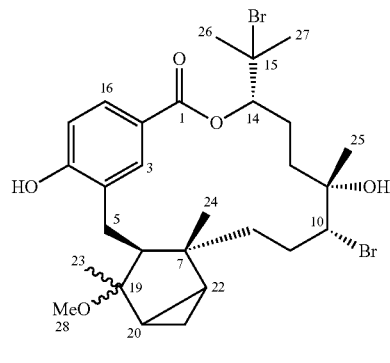

1

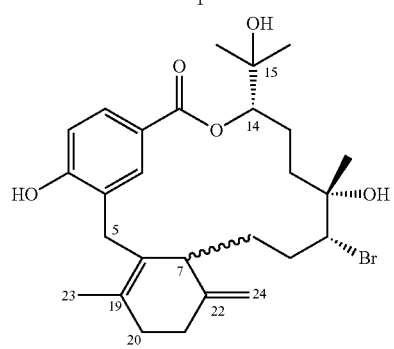

2

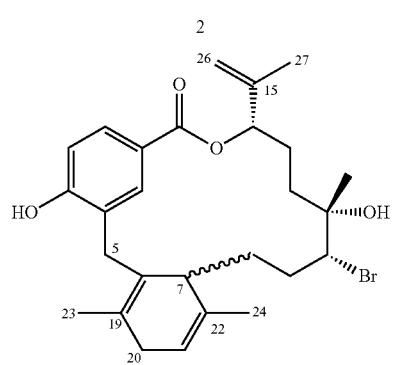

3

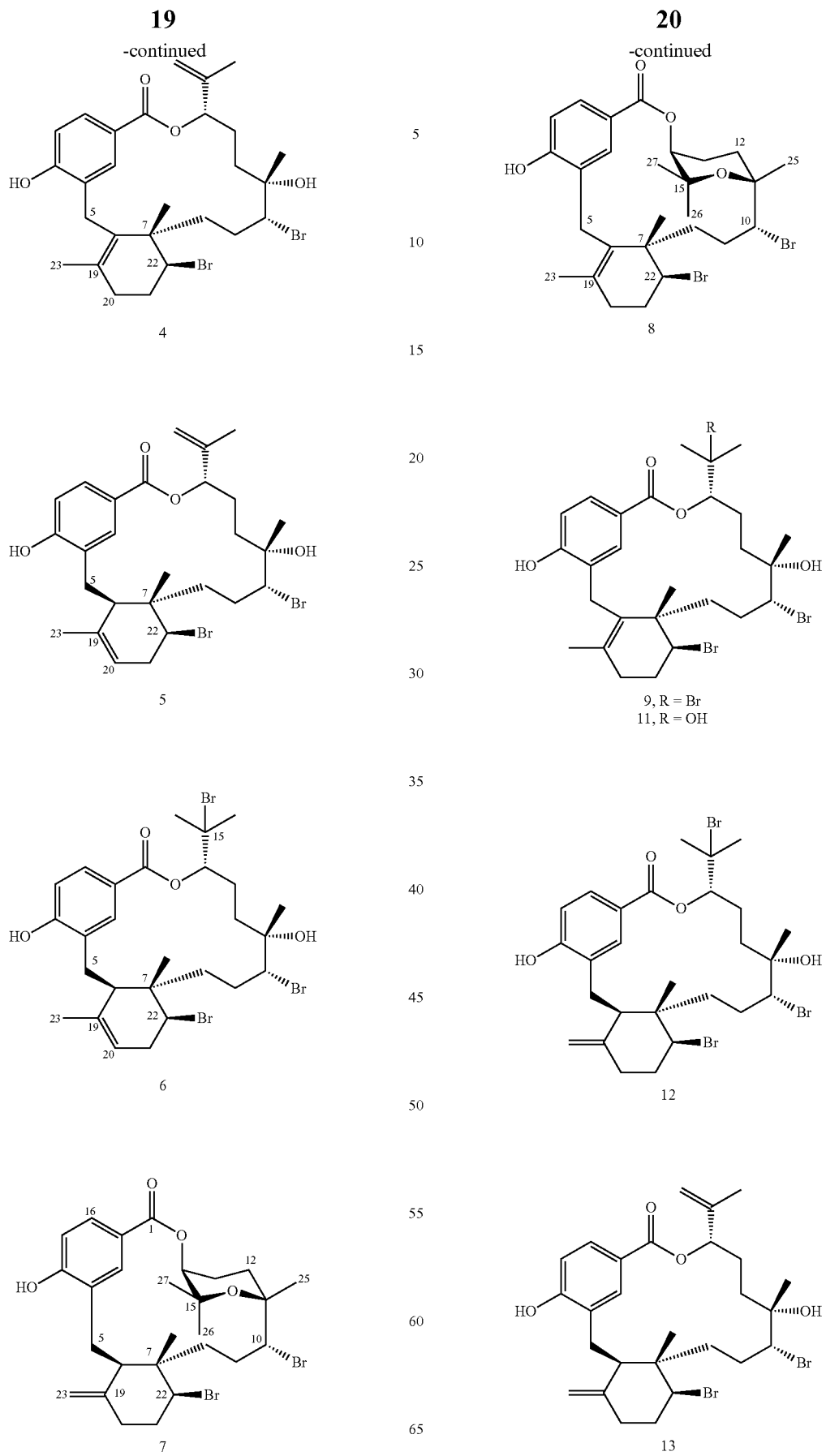

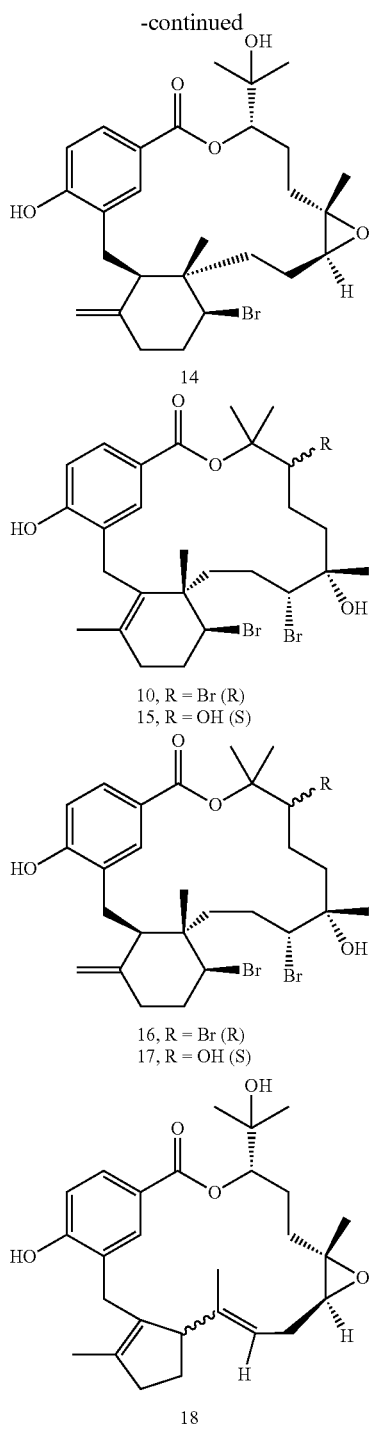

10, R = Br (R)
15, R = OH (S)

16, R = Br (R)
17, R = OH (S)

18

Following the isolation and identification of ten bromophycolides from *Callophycus serratus*, LCMS evaluation of extracts from a Yanuca (Fiji) collection of this red macroalga suggested the presence of additional bromophycolide-like metabolites. Reversed- and normal-phase HPLC yielded eight novel metabolites, bromophycolideso J-Q (1-8), in quantities sufficient for structure elucidation.

A molecular formula of $C_{28}H_{40}O_5Br_2$ was established for bromophycolide J (1), based on a mass spectral parent ion at m/z 613.1160, supported by a dibrominated isotopic splitting pattern. Inspection of $^1H$, $^{13}C$, HSQC, HMBC, and COSY NMR spectral data for 1 revealed a 4-hydroxybenzoyl group common to all bromophycolides. Comparison of spectral data for 1 with bromophycolide A (9) supported a bromine-substituted isopropyl group at the diterpene head and established diterpene-aryl connectivity identical to that of 9. Further comparison of NMR spectral data for 1 and 9 revealed substantial differences between these two natural products only in the vicinity of the carbocyclic terpene ring. For 1, HMBC correlations from Me-23 (δ 1.38) to C-6 (δ 45.5), C-19 (δ 89.8), and C-20 (δ 28.0) established C-6-C-19-C-20 connectivity. An HMBC correlation from OMe-28 (δ 3.33) to C-19 established quaternary C-19 as the site of attachment for OMe-28 and Me-23. HMBC correlations from Me-24 (δ 0.55) to C-6, C-7 (δ 45.8), and C-22 (δ 31.9) established connectivity between these carbons. COSY correlations between H-22 (δ 1.14) and both H-21 protons (δ 0.31, 0.42), between H-20 (δ 1.55) and both H-21 protons, and between H-22 and H-20, as well as the shielded chemical shift observed for methylene C-21 ($^{13}C$ δ 8.5) prompted assignment of a cyclopropyl moiety comprised of C-20, C-21, and C-22. HMBC and COSY correlations established connection between this ring system and the benzoate system via C-5, analogous to previously identified metabolites. (Kubanek et al. *J. Nat. Prod.* 2006; 69:731-735; Kubanek et al. *Org. Lett.* 2005; 7:5261-5264)

Stereochemical assignments for 1 were facilitated by comparison of $^1H$-$^1H$ scalar couplings and NOE correlations with 9. Observation of predicted scalar couplings and NOE correlations for 1 prompted assignment of 10R, 11S, 14S stereochemistry as for 9, whose absolute configuration was previously established by X-ray crystallography. Given a proposed, common biogenesis and an observed NOE between H-5b (δ 2.69) and Me-24, it seemed highly probable that a 7R configuration would also be shared between 1 and 9. NOE correlations between H-6 (δ 2.59) and H-20, but not between H-6 and Me-24, established a 6S stereocenter. This assignment matched absolute configurations reported for all bromophycolides bearing a stereocenter at this site (e.g., bromophycolide D (12)). Due to difficulties assigning stereochemistry of 5-membered rings from NOE data, the configurations of C-19, C-20, and C-22 were not assigned at this time.

Bromophycolide K (2) was assigned a molecular formula of $C_{27}H_{37}O_5Br$ from the parent ion observed at m/z 519.1767 ([M–H]$^-$). Comparison of $^1H$, $^{13}C$, HSQC, HMBC, and COSY NMR spectral data with known bromophycolides confirmed a 15-membered macrolide framework analogous to 1 and 9. For 2, a hydroxy substituent was assigned at C-15 (δ 72.1) on the basis of $^{13}C$ NMR chemical shift precedents. As with 1, HMBC and COSY correlations suggested that 2 diverged from other bromophycolides within the terpene carbocyclic moiety. Within this group, observation of HMBC correlations from Me-23 (δ 1.91) to C-6 (δ 138.6), C-19 (δ 132.7), and C-20 (δ 36.7) and from H-5a (δ 3.29) to C-7 (δ 50.6) established the tetrasubstituted olefin. COSY correlations from both H-20 protons (δ 2.24, 2.37) to both H-21 protons (δ 1.95, 2.17) and HMBC correlations from both H-24 protons (δ 4.46, 4.66) to C-7 and C-21 (δ 36.0) closed the six-membered ring containing exoand endocyclic double bonds.

High resolution mass spectral data indicated that bromophycolide L (3) differed from 2 by a loss of one $H_2O$ molecule, displaying an [M–H]$^-$ m/z of 501.1677, appropriate for a molecular formula of $C_{27}H_{35}O_4Br$. HMBC correlations from Me-27 (δ 1.79) to C-14 (δ 74.9), C-15 (δ 140.7), and C-26 (δ 111.5) suggested an isopropenyl diterpene head identical with that of bromophycolide E (13). Likewise, HMBC correlations from both H-26 vinyl protons (δ 4.98, 5.07) to C-14, C-15, and C-27 (δ 19.5) confirmed this connectivity. Evaluation of $^1$H, COSY, and HMBC NMR spectral data of 3 to that of 2 indicated an additional difference within the terpene carbocyclic system. HMBC correlations from Me-24 (δ 1.38) to C-7 (δ 49.0), C-21 (δ 122.5), and C-22 (δ 138.8) suggested that the rearranged terpene skeleton was present as in 2; however, the unsaturation was determined to be endocyclic at $\Delta^{21,22}$ through COSY correlations of olefinic H-21 (δ 4.81) with H-20b (δ 2.42) and a weak long range COSY correlation between H-21 and Me-24.

For 3, similar NOEs were observed as for bromophycolide E (13), suggesting a 10R, 11S, 14S configuration. NOEs were present between H-7 (δ 3.41) and H-20b, located 1,4 relative to each other across their six-membered ring, thus suggesting a pseudo-boat conformation of this ring. The lack of stereocenters near C-7 prevented stereochemical assignment at this position in either 2 or 3, given that an R or S configuration would be expected to result in NOEs between the axial protons H-7 and H-20b.

Bromophycolide M (4) exhibited a molecular formula of $C_{27}H_{36}O_4Br_2$ ([M−H]$^-$ m/z 581.0906), isomeric to 13. A combination of 1D and 2D NMR spectral data for 4 supported assignment of a carbon skeleton and most functionalities identical to that of 13. For 4, HMBC correlations from Me-23 (δ 1.41) to fully substituted olefinic carbons C-6 (δ 130.8) and C-19 (δ 132.6) as well as to C-20 (δ 32.4) suggested regioisomerization of the carbon-carbon double bond relative to 13. Finally, 7S, 10R, 11S, 14S, 22S stereochemistry was proposed for 4, based on comparison of NOE correlations with those of 9 and 13.

The mass spectrum of bromophycolide N (5), with [M−H]$^-$ m/z of 581.0907, suggested yet another regioisomer of 13, with a molecular formula of $C_{27}H_{36}O_4Br_2$. Comparison of $^1$H, COSY, and HMBC NMR spectral data of 5 with that of 4 and 13 suggested a difference in the cyclohexenyl double bond. HMBC correlations observed from Me-23 (δ 1.50) to C-6 (δ 47.8), C-19 (δ 137.2), and C-20 (δ 120.3), along with COSY correlations between both H-5 protons (δ 2.60, 2.83) and H-6 (δ 2.67), supported the $\Delta^{19,20}$ assignment. Because similar NOEs were observed for 5 as for 4 and 13, 6R, 7S, 10R, 11S, 14S, 22S stereochemistry was proposed for 5.

Bromophycolide O (6) exhibited an [M−H]$^-$ m/z of 661.0182 with a tribrominated isotopic pattern, appropriate for a molecular formula of $C_{27}H_{37}O_4Br_3$ as seen with bromophycolides A (9), B (10), and D (12). Inspection of 1D and 2D NMR spectral data of 6 suggested yet another 15-membered macrocyclic skeleton. As with 5, regioisomerization of the cyclohexenyl double bond to $\Delta^{19,20}$ was supported by observation of HMBC correlations from Me-23 (δ 1.65) to C-6 (δ 43.7), C-19 (δ 135.8), and C-20 (δ 119.4), as well as COSY correlations between H-5a (δ 2.82) and H-6 (δ 2.84) and a long-range COSY correlation between Me-23 and H-20 (δ 5.33). Similar NOEs were observed for 6 as with 9 and 12, thus a 6R, 7S, 10R, 11S, 14S, 22S stereochemistry was inferred for 6.

Bromophycolide P (7) also displayed the same mass spectral parent ion as 4, 5 and 13, with an [M−H]$^-$ m/z ion of 581.0865, appropriate for a molecular formula of $C_{27}H_{36}O_4Br_2$. Comparison of spectral data of 7 with other known bromophycolides supported another 15-membered macrocycle. HMBC correlations from both H-23 protons (δ 4.89, 5.30) to C-6 (δ 51.5) and C-20 (δ 37.5), as well as correlations from both H-5 protons (δ 2.61, 3.17) to C-6 and C-19 (δ 145.7), indicated the presence of an exo-methylene group (C-23, δ 110.5). Interestingly, carbon chemical shifts of 7 significantly differed from other known C. serratus natural products at C-12 (δ 26.5) and C-13 (δ 21.8). Having assigned all olefinic carbons and protons, one ring remained unaccounted for in 7 based on the index of hydrogen deficiency; thus a third six-membered ring was assigned via an ether linkage between C-11 (δ 76.0) and C-15 (δ 74.4), which accounted for the differences seen in the carbon chemical shifts at C-12 and C-13. Moreover, the phenolic hydroxyl proton (δ 5.68) was observed in the $^1$H NMR spectrum, providing evidence that the ether linkage did not involve this position (C-18, δ 156.9). However, another possibility was that rather than an ether linkage, both C-11 and C-15 were hydroxylated, and the ESIMS ion observed at m/z 581.0865 resulted from dehydration at C-11 or C-15 during ionization. In order to test this hypothesis, 7 was acetylated, and then subjected to $^1$H NMR spectroscopy (data not shown). Only one acetyl group was observed in the $^1$H NMR spectrum, rejecting the notion of a polyhydroxylated natural product and confirming the presence of a single free, phenolic hydroxyl group along with the tetrahydropyran ring in 7.

Retention of the 6R, 7S, 10R, 22S configuration of 7 was proposed by comparison of NOEs for 7 with other bromophycolides possessing the C-19-C-23 unsaturation (e.g. 12-14, 16-17, and by inferring a common biosynthetic origin. NOEs observed between H-14 (δ 5.08) and both H-13s (δ 1.88, 2.30), Me-26 (δ 1.36), and Me-27 (δ 1.09) suggested an equatorial position for H-14 within the tetrahydropyran ring of 7. Furthermore, 1,3-diaxial NOE correlations were observed between H-13b and Me-26. NOEs were also seen between equatorial Me-25 (δ 1.47) and both H-12 protons (δ 1.72, 2.35). Collectively, these data supported a configuration of 11R, 14S for 7.

High resolution mass spectral data of bromophycolide Q (8), [M−H]$^-$ m/z 581.0869, suggested a molecular formula of $C_{27}H_{36}O_4Br_2$, as for 4-5, and 7. The $^1$H NMR spectral data for 8 were identical to that of 7, except for the loss of the exomethylene signals and the presence of one additional methyl group. HMBC correlations from H-5a (δ 3.15) to olefinic carbons C-6 (δ 131.0) and C-19 (δ 132.9), as well as from Me-23 (δ 1.34) to C-6, C-19 and C-20 (δ 32.6) suggested regioisomerization of the double bond in 8 relative to 7. A configuration of 7S, 10R, 11R, 14S, 22S stereochemistry was proposed for 8 based on similar NOEs observed for 7 and 8.

Together, bromophycolides J-Q (1-8) represent two novel carbon skeletons, two unique tetrahydropyran-containing bromophycolides, plus two regioisomers of previously reported bromophycolide E (13) and a regioisomer of bromophycolide A (9). Among the 28 known natural products from C. serratus, bromophycolide J (1) is unique as the only methoxy-substituted metabolite as well as the only bromophycolide bearing a bicyclo[3.1.0] hexane ring in a new carbon skeleton. However, the bicyclo [3.1.0] hexane ring in 1 could have arisen as an artifact from methanolysis of 6, initiated by cleavage of the C-22-Br bond followed by a ring closure of the bicyclo[3.1.0] hexane by homoallylic substitution of bromine by methanol. Bromophycolides K (2) and L (3) represent a second novel carbon skeleton, differing from known bromophycolide structural motifs by a proposed biosynthetic 1,2-methyl shift. Both methyl and hydride shifts are common in terpene biosynthesis; however, 2 and 3 represent the first bromophycolides exhibiting a rearranged carbon skeleton. Bromophycolides P (7) and Q (8) are also structurally distinct from the other natural products of this class, each with a tetrahydropyran ring within the macrocycle that significantly increases the hydrophobicity and conformational rigidity of the molecule. All of these structural features, including stereochemistry, may be accounted for with biosynthetic mechanisms that incorporate the same bromonium intermediate previously suggested for five- and six-membered ring cyclizations in bromophycolides. The tetrahydropyran ring in 7-8 could arise from attack of nucleophilic C-15 hydroxyl on an electrophilic bromonium ion intermediate at C-10-C-11. Another possible biosynthetic route could involve bromohydrin formation at C-10-C-11, as in other bromophycolides, followed by attack of the C-11 hydroxyl onto a C-15 carbocation. The structural novelty observed among the diterpene systems within these 28 natural products suggests a high biosynthetic flexibility within this group.

Bromophycolides J-Q (1-8) exhibited low micromolar activities against the most common and deadly human malaria parasite, *Plasmodium falciparum* (malaria tropica), prompting evaluation of antimalarial activities for previously reported bromophycolides A-I (9-17) and debromophycolide A (18, Table 1). Bromophycolides A (9), D (12), E (13), H (16), and M (4), representing both 15- and 16-membered lactone frameworks, exhibited potent antimalarial activity with $IC_{50}$'s of 0.3-0.9 µM, suggesting that neither mode of lactonization confers an inherent bioactivity advantage.

TABLE 1

Antimalarial activities of bromophycolides J-Q (1-8) and previously reported bromophycolides A-I (9-17) and debromophycolide A (18).

| Compound | Antimalarial $IC_{50}$ (µM) |
|---|---|
| 1 | 2.7 |
| 2 | 44 |
| 3 | 9.8 |
| 4 | 0.5 |
| 5 | 1.4 |
| 6 | 1.4 |
| 7 | 2.9 |
| 8 | 1.4 |
| 9 | 0.9 |
| 10 | 4.8 |
| 11 | 56 |
| 12 | 0.3 |
| 13 | 0.8 |
| 14 | 18 |
| 15 | 14 |
| 16 | 0.9 |
| 17 | 2.5 |
| 18 | >100 |

Furthermore, a macrolide motif appears to be essential for antimalarial activity, considering that non-macrocyclic callophycoic acids and callophycols also isolated from *C. serratus* were less active against *P. falciparum*. Lane et al., *J. Org. Chem.* 2007; 72:7343-7351.

Current natural product-derived antimalarial drugs include the artemisinines and quinines, of terpene and alkaloid biogenesis, respectively. Schlitzer, *Arch. Pharm. Chem. Life Sci.* 2008; 341:149-163. Artemisinines are the most active and rapid-acting antimalarial agents known today ($IC_{50}$ values <7 nM) and are also cytotoxic to certain types of human cancer cells. Singh et al., *Anticancer Res.* 2004; 24:2277-2280. While multiple treatment options are available, many malaria strains have evolved drug resistance over the past half-century; also, prophylactic drugs remain obscure, thus making the need for new treatments an immediate concern. The 15- and 16-membered bromophycolide frameworks described here also represent a new scaffold from which novel and potent antimalarial drugs could be developed.

Of the newly discovered compounds, bromophycolides P (7) and Q (8) exhibited the most potent antibacterial activity against methicillin-resistant *Staphylococcus aureus* (MRSA) and vancomycin-resistant *Enterococcus faecium* (VREF, Table 2), suggesting that the conformational rigidity and/or hydrophobicity conferred by the tetrahydropyran system contributes to antibacterial activity. While all tested bromophycolides exhibited moderate antineoplastic activity, only 5 displayed some cell line selectivity, with an $IC_{50}$ of 1.5 µM against the breast tumor cell line DU4475, the most sensitive cancer tested (Table 2). Interestingly, while 5 demonstrated cancer cell line selectivity, its regioisomer 4 was quite active against all cancer cell lines tested ($IC_{50}$'s 2.1-7.2 µM). Bromophycolide Q (8) was the most potent *C. serratus* natural product evaluated (mean anticancer $IC_{50}$ value of 2.0 µM), but showed little cell line selectivity.

TABLE 2

Pharmacological activities of bromophycolides J-Q (1-8).

| Cmpd | antibacterial activity (µM) | | Antitubercular | anticancer activity (µM) | | cell line selectivity ($IC_{50}$ max/$IC_{50}$ min) | antifungal activity $IC_{50}$ (µM)[c] |
|---|---|---|---|---|---|---|---|
|  | MRSA $IC_{50}$ | VREF $IC_{50}$ | MIC | mean[a] | DU4475[b] |  |  |
| 1 | 80 | 66 | 94 | 10 | 3.3 | 10 | NT |
| 2 | NT | NT | NT | 31 | 18 | 3.6 | NT |
| 3 | 8.2 | 26 | 49 | NT | NT | — | 46 |
| 4 | 6.7 | 21 | >100 | 3.1 | 2.1 | 3.5 | >90 |
| 5 | 7.2 | 56 | >50 | 8.6 | 1.5 | 15 | 44 |
| 6 | 8.9 | 18 | NT | 9.7 | 7.3 | 3.5 | >75 |
| 7 | 1.4 | 13 | 48 | 7.9 | 21 | 4.5 | 45 |
| 8 | 1.8 | 5.8 | 22 | 2.0 | 2.0 | 5.5 | >90 |

[a]Mean of 12 cancer cell lines (see Experimental section for details)
[b]breast tumor cell line
[c]Using amphotericin-resistant *Candida albicans*
NT indicates not tested due to insufficient material The current study expands the number of bioactive diterpene benzoate metabolites from *Callophycus serratus* and includes two additional novel carbon skeletons, thus suggesting that unexplored red algal families could be an untapped resource of biologically active and interesting natural products.

*Callophycus serratus* (Harvey ex Kutzing 1957) (family Solieriaceae, order Gigartinales, class Rhodophyceae, phylum Rhodophyta) was collected from Yanuca in the Fiji Islands (18° 23' 57" S, 177° 57' 59" E). Samples were frozen at −20° C. until extraction. Voucher specimens were identified by comparison with previously described morophological traits, (Littler et al., *South Pacific Reef Plants*. Offshore Graphics, Inc.; Washington, D.C.: 2003) preserved in aqueous formalin, and deposited at the University of the South Pacific in Suva, Fiji and at Georgia Institute of Technology as ICBG-G-0004, ICBG-G-0005, ICBG-G-0021, and ICBG-G-0049.

Frozen *Callophycus serratus* was extracted successively with water, methanol, and methanol/dichloromethane (1:1 and 1:2). Extracts were combined, reduced in vacuo, and subjected to liquid partitioning between methanol/water (9:1) and petroleum ether. The methanol/water ratio of the aqueous fraction was then adjusted to 3:2 and this fraction partitioned against chloroform. The chloroform fraction was subjected to multiple rounds of reversed-phase $C_{18}$ HPLC (using Agilent Zorbax SB-$C_{18}$, 5 μm, 9.4×250 mm or Alltech Alltima $C_{18}$, 5 μm, 10×250 mm) with a gradient of acetonitrile/water and methanol/water mobile phases, followed by normal phase silica HPLC (using Agilent RX-SIL columns, 5 μm, 9.4×250 mm) with isocratic hexanes/ethyl acetate (82:18) to yield bromophycolides J-Q (1-8). All NMR spectra were collected in $CDCl_3$ and referenced to residual $CHCl_3$ (δ 7.24 and 77.0 ppm for $^1H$ and $^{13}C$, respectively).

All pharmacological assays were performed as previously described (Kubanek et al., *J. Nat. Prod.* 2006; 69:731-735; Kubanek et al., *Org. Lett.* 2005; 7:5261-5264; Lane et al., *J. Org. Chem.* 2007; 72:7343-7351). Briefly, antimalarial activity was determined with a SYBR Green based parasite proliferation assay, adapted from Smilkstein (*Antimicrob. Agents Ch.* 2004; 48:1803-1806) and Bennett (*Antimicrob. Agents Ch.* 2004; 48:1807-1810). *Plasmodium falciparum* parasites (3D7 strain MR4/ATCC, Manassas, Va.) were cultured in human O+ erythrocytes as previously described (Trager et al., *Science.* 1976; 193:673-675).

Antibacterial assays were performed using methicillin-resistant *Staphylococcus aureus* (MRSA, ATCC 10537) and vancoymcin-resistant *Enterococcus faecium* (VREF, ATCC 12952) as test pathogens. Vancomycin and chloramphenicol were used as positive controls for MRSA and VREF, respectively, and DMSO was used as negative control. The optical density was measured at 600 nm using a microplate reader, and the $IC_{50}$ of each compound was calculated using the dose concentration at 50% inhibition on a sigmoidal dose response curve generated using GraphPad Prism version 4.00 for Windows, GraphPad software, San Diego, Calif., USA.

Amphotericin B-resistant *Candida albicans* (ATCC 90873) was used in the antifungal assays. A mixed nystatin/amphotericin B solution was used as a positive control, and DMSO was used as negative control. The optical density was then measured at 600 nm using a microplate reader and the $IC_{50}$ was calculated for each in the same method as the antibacterial assays.

Antitubercular activity was assessed against *Mycobacterium tuberculosis* strain H37Rv (ATCC 27294) using the microplate alamar blue assay (MABA) as described previously (Falzari et al., *Antimicrob. Agents Ch.* 2005; 49:1447-1454). Compounds 1 and 4 were tested at a maximum concentration of 100 μM, and 3, 5, 7-8 were tested at a maximum concentration of 50

Bromophycolides J (1), K (2) and M-Q (4-8) were evaluated against a panel of 12 tumor cell lines including breast, colon, lung, prostate, and ovarian cancer cells. Specific cell lines were: BT-549, DU4475, MDA-MD-468, PC-3, SHP-77, LNCaP-FGC, HCT116, MDA-MB-231, A2780/DDP-S, Du145, CCRF-CEM, and A549. In vitro cytotoxicity was tested with the (3-(4,5-dimethylthiazol-2-yl)-5-(3-carboxylmethoxyphenyl)-2-(4-sulfophenyl)-2H-tetrazolium inner salt) MTS dye conversion assay as described previously (Falzari et al., *Antimicrob. Agents Ch.* 2005; 49:1447-1454).

Bromophycolide J (1)

white amorphous solid (1.0 mg; 0.023% plant dry mass); $[\alpha]^{23}_D$ +35 (c 0.057 g/100 mL, MeOH); UV (MeOH) $\lambda_{max}$ (log ε) 265 (3.78) nm; $^1H$ NMR ($CDCl_3$, 500 MHz) and $^{13}C$/DEPT NMR ($CDCl_3$, 125 MHz) data; NOE, COSY, HMBC NMR data; HRESIMS [M−H]− m/z 613.1160 (calcd for $C_{28}H_{39}O_5Br_2$, 613.1164).

Bromophycolide K (2)

white amorphous solid (0.8 mg; 0.018% plant dry mass); $[\alpha]^{23}_D$ +22 (c 0.046 g/100 mL, MeOH); UV (MeOH) $\lambda_{max}$ (log ε) 264 (3.54) nm; $^1H$ NMR ($CDCl_3$, 500 MHz) and $^{13}C$/DEPT NMR ($CDCl_3$, 125 MHz) data; NOE, COSY, HMBC NMR data; HRESIMS [M−H]− m/z 519.1767 (calcd for $C_{27}H_{36}O_5Br$, 519.1746).

Bromophycolide L (3)

white amorphous solid (0.3 mg, 0.007% plant dry mass); $[\alpha]^{24}_D$ +70 (c 0.033 g/100 mL, MeOH); UV (MeOH) $\lambda_{max}$ (log ε) 262 (3.72) nm; $^1H$ NMR ($CDCl_3$, 500 MHz) and C NMR ($CDCl_3$, 125 MHz) data; NOE, COSY, and HMBC NMR data; HRESIMS [M−H]− m/z 501.1677 (calcd for $C_{27}H_{34}O_4Br$, 501.1640).

Bromophycolide M (4)

white amorphous solid (1.8 mg; 0.041% plant dry mass); $[\alpha]^{23}_D$ +68 (c 0.10 g/100 mL, MeOH); UV (MeOH)$\lambda_{max}$ (log ε) 262 (3.66) nm; $^1H$ NMR ($CDCl_3$, 500 MHz) and $^{13}C$/DEPT NMR ($CDCl_3$, 125 MHz) data; NOE, COSY, HMBC NMR data; HRESIMS [M−H]− m/z 581.0906 (calcd for $C_{27}H_{35}O_4Br_2$, 581.0902).

Bromophycolide N (5)

white amorphous solid (1.0 mg, 0.023% plant dry mass); $[\alpha]^{24}_D$ +101 (c 0.033 g/100 mL, MeOH); UV (MeOH) $\lambda_{max}$ (log ε) 260 (3.42) nm; $^1H$ NMR ($CDCl_3$, 500 MHz) and $^{13}C$/DEPT NMR ($CDCl_3$, 125 MHz) data; NOE, COSY, and HMBC NMR data; HRESIMS [M−H]− m/z 581.0907 (calcd for $C_{27}H_{35}O_4Br_2$, 581.0902).

Bromophycolide O (6)

white amorphous solid (0.5 mg, 0.012% plant dry mass); $[\alpha]^{24}_D$ +88 (c 0.011 g/100 mL, MeOH); UV (MeOH) $\lambda_{max}$ (log ε) 260 (3.54) nm; $^1H$ NMR (CDCl, 500 MHz) and $^{13}C$ NMR ($CDCl_3$, 125 MHz) data; NOE, COSY, and HMBC NMR data; HRESIMS [M−H]− m/z 661.0182 (calcd for $C_{27}H_{36}O_4Br_3$, 661.0169).

Bromophycolide P (7)

white amorphous solid (4.0 mg, 0.092% plant dry mass); $[\alpha]^{24}_D$ +120 (c 0.05 g/100 mL, MeOH); UV (MeOH) $\lambda_{max}$ (log ε) 260 (4.02) nm; $^1H$ NMR (CDCl, 500 MHz) and $^{13}C$ NMR ($CDCl_3$, 125 MHz) data; NOE, COSY, and HMBC NMR data; HRESIMS [M−H]− m/z 581.0865 (calcd for $C_{27}H_{35}O_4Br_2$, 581.0902).

Bromophycolide Q (8)

white amorphous solid (1.0 mg, 0.023% plant dry mass); $[\alpha]^{24}_D$ +102 (c 0.03 g/100 mL, MeOH); UV (MeOH) $\lambda_{max}$ (log ε) 260 (3.83) nm; $^1$H NMR (CDCl, 500 MHz) and $^{13}$C NMR (CDCl$_3$, 125 MHz) data; NOE, COSY, and HMBC NMR data; HRESIMS [M−H]$^−$ m/z 581.0869 (calcd for C$_{27}$H$_{35}$O$_4$Br$_2$, 581.0902).

EXAMPLE 2

Bromophycolides R-U and Biological Activities

Four new bromophycolides, R-U (1-4), were isolated from the Fijian red alga *Callophycus serratus* and were identified by 1D and 2D NMR and mass spectroscopic analyses. These compounds expand the known structural variety of diterpenebenzoate macrolides and exhibited modest cytotoxicity toward selected human cancer cell lines. Bromophycolide S (2) also showed submicromolar activity against the human malaria parasite *Plasmodium falciparum*.

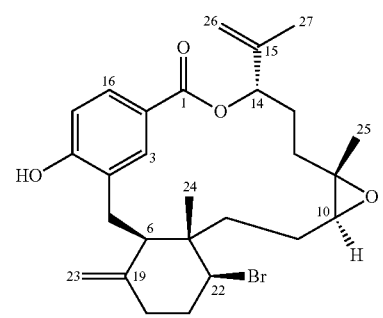

1

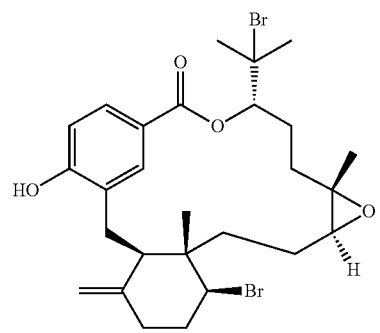

2

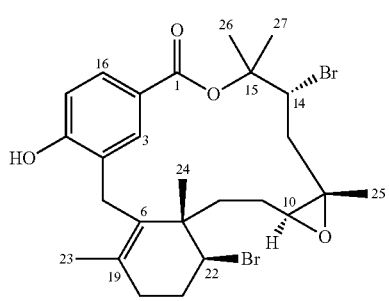

3

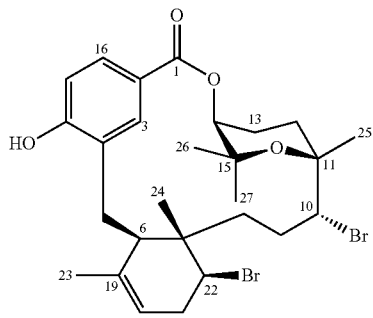

4

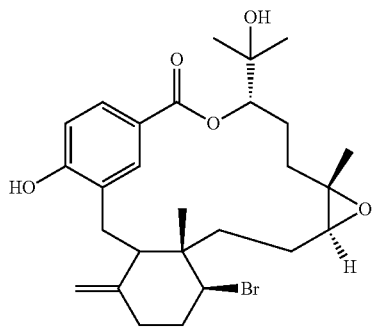

5

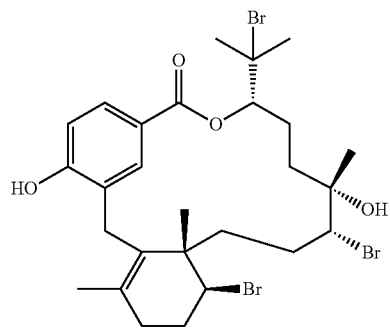

6

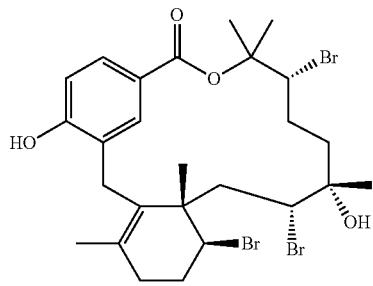

7

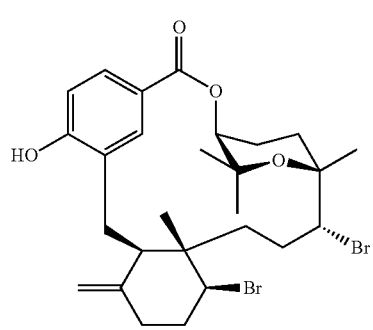

8

*Callophycus serratus* is a marine red alga that lives on rocky floors of caves and on undercut walls at depths of 3-20 m throughout the tropical and subtropical Pacific Ocean. Littler et al., *South Pacific Reef Plants*; Offshore Graphics, Inc.: Washington, D.C., 2003; p 90. Recent reviews have demonstrated that secondary metabolites from red algae are dominated by terpenes and halogenated polyphenols, which exhibit multiple types of biological activity. Blunt et al., *Nat. Prod. Rep.* 2009, 26, 170-244; Stout et al., *Comprehensive Natural Products Chemistry*, 2nd ed.; *Marine Macroalgal Natural Products*; Elsevier: New York, 2010; Vol. 2. Investigations of *C. serratus* from Fijian coral reefs has resulted in the discovery of 18 novel diterpene-benzoate macrolides (bromophycolides A-Q and debromophycolide A), eight diterpene-benzoic acids (callophycoic acids A-H), and two diterpene phenols (callophycols A, B), several of which possessed antimalarial, antibacterial, antitubercular, anticancer, and antifungal activities. See Example 1 above.

Extracts of *C. serratus* were separated by liquid-liquid partition to give four fractions (see Extraction and Isolation). The $CHCl_3$-soluble fraction was further separated by reversed-phased HPLC to yield four new bromophycolides (R-U, 1-4), which were identified by NMR and mass spectrometric analyses.

Bromophycolide R (1), isolated as a white powder, showed a HR-ESIMS molecular ion peak at m/z [M+H]+ of 503.1824, corresponding to a molecular formula of $C_{27}H_{35}BrO_4$ and supported by a monobrominated isotopic splitting pattern. The UV spectrum had an absorption maximum at 262 nm common to reported bromophycolides. In the $^1$H NMR spectrum of 1, an ABX coupling system at δ 8.30 (br s), 7.66 (dd, J) 8.5, 1.5 Hz), and 6.72 (d, J) 8.0 Hz) was in good agreement with the p-hydroxybenzoate ester portion of previously isolated bromophycolides. $^{13}$C NMR signals at δ 111.6 (C-26) and 144.3 (C-15) suggested a vinyl group. Both $H_2$-26 vinyl protons (δ 4.90, 5.02) correlated to C-27 (δ 18.4) and C-14 (δ 78.7) in the HMBC spectrum, revealing an isopropenyl diterpene head. Four isoprene units were suggested by HMBC correlations from Me-27 (δ 1.78) to C-14, C-15, and C-26; from Me-25 (δ 1.34) to C-10 (δ 67.2), C-11 (δ 64.1), and C-12 (δ 32.9); from Me-24 (δ 0.96) to C-7 (δ 43.8), C-8 (δ 36.0), and C-22 (δ 63.3); and from both H2-23 protons (δ 4.76, 4.81) to C-6 (δ 46.0) and C-20 (δ 37.9). The head-to-tail linkages of the isoprene units were established through COSY correlations between H-13b (δ 2.05) and H-12a (δ 1.16); H-9a (δ 1.63) and H-8a (δ 1.91); and H-21a (δ 2.08) and H-20a (δ 2.23). An HMBC correlation from Me-24 to C-6 closed the C-6-C-7 linkage of the six-membered ring. Given the fact that only one oxygen atom was not already assigned, the two upfield shifted carbinol signals at C-10 and C-11 suggested an epoxide and accounted for the final degree of unsaturation. The remaining bromine was assigned at C-22, consistent with other previously identified bromophycolides. Bromophycolide R (1) is the dehydrated form of previously reported bromophycolide F (5), resulting in the isopropenyl terpene head of 1.

Configurational assignments for 1 were facilitated by ROESY spectroscopic data and previously reported X-ray crystallographic data of bromophycolide A (6). NOE correlations between H-6 (δ 3.45) and H-22 (δ 4.61), together with correlations between Me-24 and both H2-5 protons (δ 2.70, 3.16), suggested 6R, 7S, 22S stereocenters. Likewise, NOE correlations between Me-25 and H-9a, along with correlations between H-10 (δ 2.83) and H-12a, supported a trans configuration at C-10 and C-11. Additional NOEs observed between H-9a and Me-24 together with NOE correlations between H-10 and H-3, H-3, and H-6 and a weak NOE between H-6 and H-10 linked the epoxide to confirmed chiral centers C-6 and C-7 and suggested a 10S, 11S configuration. H-14 (δ 4.74) showed an NOE correlation with overlapping signals at δ 1.96-1.97, assigned to H-13a and H-12b. However, NOE correlations observed between Me-25 and H-13b and between H-14 and H-13b indicated that Me-25, 1'-13b, and H-14 were on the same face of the molecule. This placed H-13a and H-12b in an anti relationship with respect to each other. Considering the large (J) 11 Hz) coupling of the broad doublet observed for H-14 indicating an anti relationship between H-14 and H-13a, the NOE observed between H-14 and an overlapping proton at δ 1.96-1.97 must be to H-12b (and not H-13a). Thus, a 14S configuration was concluded, which is consistent with previously reported bromophycolides for which X-ray crystallography established the absolute configuration.

Bromophycolide S (2) possessed a molecular formula of $C_{27}H_{36}Br_2O_4$ from the ion with m/z 605.0929 [M+Na]+, supported by a dibrominated isotopic splitting pattern, suggesting the addition of HBr relative to 1. All 13C NMR chemical shifts for 2 differed by less than 3 ppm from those of 1 except for the signals at C-14 (δ 80.4), C-15 (δ 66.9), Me-26 (δ 32.7), and Me-27 (δ 29.7), revealing a 15-membered lactone framework with a p-hydroxybenzoate structure as 1.

One fewer olefin and an additional methyl signal were found in 2, suggesting that the differences between 1 and 2 were at the diterpene head. HMBC correlations from Me-26 (δ 1.83) and Me-27 (δ 1.78) to C-15, C-14, and each other revealed two methyls at brominated carbon C-15, identical to 6. Due to the structural resemblances and similar observed NOEs between 1, 2, and 6, the configuration of 2 was assigned as 6R, 7S, 10S, 11S, 14S, 22S.

The high-resolution mass spectrum of bromophycolide T (3) displayed a molecular ion peak at m/z 605.0881 [M+Na]+, appropriate for a molecular formula of C27H36Br2O4, isomeric with 2. Comparing the 1H and 13C NMR spectra for 3 to those of 1 and 2, the p-hydroxybenzoate and the epoxy functions remained intact. HMBC correlations from H-5a (δ 3.17) to olefinic carbon C-6 (δ 131.9), as well as from Me-23 (δ 1.90) to C-19 (δ 132.8) and C-6, revealed regioisomerization of the double bond in 3 relative to 1 and 2. The connectivity between the benzoate and diterpene head was also altered, with the downfield shifted oxygenated quaternary carbon C-15 (δ 82.4) as the site of connection, as previously shown for bromophycolide B (7).4 Both diterpene head methyl groups Me-26 (δ 1.86) and Me-27 (δ 1.76) correlated with C-14 (δ 66.8), C-15, and each other in the HMBC spectrum. C-14 was further linked to the epoxide, as shown through COSY correlations between H-14 (δ 4.00) and H-13a (δ 2.10) and between H-13b (δ 2.22) and H-12a (δ 1.68) and by HMBC correlations from Me-25 (δ 1.27) to C-12 (δ 37.4).

From previously reported X-ray crystallographic data for 7 and examination of ROESY spectroscopic data, a 7S,22S configuration for 3 was suggested on the basis of NOEs observed between H-22 and H-9a and between H-9a and H-10, along with NOE correlations between H-25 and H-9b; H-9b and H-24; H-25 and H-8a; and H-8a and H-24. Similarly, NOEs observed between H-10 (δ 2.97) and H-12a and between Me-25 (δ 1.27) and H-9b (δ 1.71) suggested a 10S, 11S configuration similar to that of 1. Given the structural similarities with bromophycolide H and 7,4,5 and NOE correlations between H-14 and both Me-26 and Me-27, a 14R configuration was inferred.

The molecular formula for bromophycolide U (4) was confirmed as $C_{27}H_{36}Br_2O_4$ from the parent ion at m/z 605.0871 [M+Na]+, isobaric with 2 and 3. The $^1$H NMR spectroscopic data for 4 were similar to bromophycolides P (8) and Q. The cyclohexenyl double bond of 4 appeared to display a C-19-C-20 unsaturation identical to bromophycolide O[7] and could be confirmed by COSY correlations from H-21b (δ 2.57) to H-22 (δ 4.29) and H-20 (δ 5.17), along with HMBC correlations from Me-23 (δ 1.50) to C-6 (δ 48.1), C-19 (δ 137.0), and C-20 (δ 119.9). Considering that this is a common double-bond rearrangement with otherwise similar NMR spectroscopic data to 8 and bromophycolide Q, the configuration for 4 was proposed to be 6R,7S,10R,11R,-14S,22S.

Bromophycolides R-U (1-4) would be expected to follow a similar biosynthetic pathway to that proposed for previously reported bromophycolides. The epoxide in 1-3 would be expected to arise from an $S_N2$ nucleophilic attack of the C-11 hydroxy at C-10, displacing bromide and resulting in an inversion of configuration at C-10 and a trans epoxide. While we cannot completely rule out the possibility that epoxide formation occurred during the isolation process, experimental evidence suggests otherwise. We have found that the epoxide will not form from the bromohydrin in 6 at temperatures less than 50° C. nor without the presence of base. Thus, given that our isolation occurred at or below 25° C. and at relatively neutral pH, the likelihood that the epoxides were formed during the isolation process is low.

Bioactive compounds 1-4 exhibited moderate activity against the human malarial parasite *Plasmodium falciparum* with IC50 values ranging from 0.9 to 8.4 µM (Table 3). The antimalarial activity of 2 (IC50 0.9 µM) was comparable to the most active bromophycolides reported previously. Within the 15-membered lactone framework, less polar groups at the diterpene head appear to be associated with potency, because substitution of a bromine (as in 2 and bromophycolide D) for a hydroxy at C-15 was associated with 2-6-fold increase in activity, and bromophycolides possessing an isopropenyl group at the diterpene head (as in 1 and bromophycolide E) displayed intermediate antimalarial activity. The tetrahydropyran ring of 4, 8, and bromophycolide Q (IC50 1,4-2.9 µM) contributed to reduced activity compared to open forms. In both the 15- and 16-membered lactone frameworks, the epoxide at C-10 (1-3) contributed to reduced antimalarial activity compared to the bromohydrin function (7, bromophycolides D and E) at C-10-C-11.7 The antibacterial, antifungal, and anticancer activities of 1-4 were also analyzed (Table 3). The results were similar to those of previously reported bromophycolides.

malarial activity and suggests possibilities for the design and synthesis of antimalarial drugs.

General procedures. Optical rotations were measured on a Jasco P-1010 spectropolarimeter. UV spectra were recorded in methanol with a Spectronic 21D spectrophotometer. IR spectra were recorded on a Shimadzu FTIR 8400S spectrophotometer. NMR spectra were acquired on a Bruker DRX-500 instrument, using a 5 mm broadband or inverse detection probe for 1H, 13C, 1H-1H COSY, HSQC, HMBC, NOESY, and ROESY experiments. For some compounds, quaternary carbon chemical shifts were inferred from HMBC data. High-resolution mass spectra were generated using electrospray ionization with an Applied Biosystems QSTAR-XL hybrid quadrupole timeof-flight tandem mass spectrometer and Analyst QS software. LC-MS analyses were conducted using a Waters 2695 HPLC with Waters spectrometer with 2996 diode-array UV detection and Micromass ZQ 200 mass spectrometer with electrospray ionization. LC-MS chromatography was achieved with an Xterra NS-C18 3.5 µm column measuring 2.1×15 mm and gradient mobile phases of aqueous methanol with 0.1% acetic acid. Semipreparative HPLC was performed using a Waters 2690 pump, with a Waters 996 diode-array UV detector, controlled by Waters Millenium software. Compound purification by HPLC was achieved using Agilent Zorbax SB-C18 (5 µm, 9.4×250 mm) and Phenomenex Develosil C30 RPAQUEOUS (5 µm, 4.6×250 mm) columns All commercial chemicals were reagent grade except for solvents used for HPLC and LC-MS, which were HPLC or Optima grade (Fisher Scientific Co.). NMR solvents were purchased from Cambridge Isotope Laboratories.

Algal Material. *Callophycus serratus* (Harvey ex Kutzing 1957) (family Solieriaceae, order Gigartinales, class Rhodophyceae, phylum Rhodophyta) was collected from coral reefs offshore from Yanuca Island in Fiji (18° 23'57" S, 177° 57'59" E). Fresh samples were immediately frozen at −20° C. until further processed for extraction in the laboratory. Voucher specimens were identified by comparison with previously described morphological traits7 and preserved in 10% aqueous formalin. Vouchers with identification ICBG-G-0004 and ICBG-G-0593 were deposited at the University of the South Pacific in Suva, Fiji, and at Georgia Institute of Technology, Atlanta, Ga.

TABLE 3

Pharmacological Activities of Bromophycolides R-U (1-4)

| cmpd | antimalarial activity IC$_{50}$ (µM) | antibacterial activity (µM) | | | antifungal activity[a] IC$_{50}$ (µM) | anticancer activity (µM) | |
|---|---|---|---|---|---|---|---|
| | | MRSA IC$_{50}$ | VREF IC$_{50}$ | M tuberculosis MIC | | mean[b] | cell line selectivity (IC$_{50}$ max/ IC$_{50}$ min) |
| 1 | 1.7 | >15 | >15 | >50 | >15 | 19 | 2.9 |
| 2 | 0.9 | >15 | 3.8 | 23 | >15 | 16 | 2.2 |
| 3 | 8.4 | >15 | >15 | >50 | >15 | 24 | 1.6 |
| 4 | 2.1 | 0.9 | 0.9 | 22 | >15 | 16 | 3.1 |

[a]Using amphotericin-resistant *Candida albicans*.
[b]Mean of 12 cancer cell lines (see the Experimental Section for details).
MRSA = methicillin-resistant *Staphylococcus aureus*.
VREF = vancomycin-resistant *Enterococcus faecium*.

Four new bromophycolides and their biological activities are described. This study not only expands the number of discovered diterpene-benzoate macrolides from *C. serratus*, but also explores the structure-activity relationship for anti- Extraction and Isolation. Freeze-dried *C. serratus* was extracted with MeOH five times. The extracts were combined, reduced under vacuum, and sequentially partitioned between MeOH/H2O (9:1) and petroleum ether. The aqueous fraction was adjusted to MeOH/H2O (3:2) and partitioned against CHCl3. The CHCl3-soluble fraction was separated by column chromatography using HP20ss resin, starting with MeOH/H2O (3:2) and eluting with MeOH (100%). Further purification by C30 reversed-phase HPLC with 84% aqueous MeOH afforded bromophycolides R-U (1-4). Pure compounds were analyzed by LCMS to determine λmax and molecular mass and quantified by 1H NMR spectroscopy using 2,5-dimethylfuran as internal standard.

Bromophycolide R (1): white, amorphous solid (0.57 mg, 0.0029% dry mass); [R]23D +118 (c 0.038, MeOH); UV (MeOH) λmax (log ε) 260 (3.52) nm; IR (NaCl) νmax 3356, 2926, 1717, 1603, 1456, 1273, 1119 cm-1; 1H NMR (CDCl3, 500 MHz) and 13C NMR (CDCl3, 125 MHz) data; 2D NMR data; HRESIMS [M+H]+m/z 503.1824 (calcd for C27H36BrO4, 503.1797).

Bromophycolide S (2): white, amorphous solid (1.2 mg, 0.0062% dry mass); [R]23D +66 (c 0.076, MeOH); UV (MeOH) λmax (log ε) 260 (3.53) nm; IR (NaCl) νmax 3366, 2930, 1715, 1600, 1454, 1273, 1111 cm-1; 1H NMR (CDCl3, 500 MHz) and 13C NMR (CDCl3, 125 MHz) data; 2D NMR data; HRESIMS [M+Na]+m/z 605.0929 (calcd for C27H36Br2O4Na, 605.0878).

Bromophycolide T (3): white, amorphous solid (0.58 mg, 0.0030% dry mass); [R]23D +141 (c 0.039, MeOH); UV (MeOH) λmax (log ε) 260 (3.79) nm; IR (NaCl) νmax 3375, 2918, 1717, 1601, 1458, 1279, 1115 cm-1; 1H NMR (CDCl3, 500 MHz) and 13C NMR (CDCl3, 125 MHz) data; 2D NMR data; HRESIMS [M+Na]+m/z 605.0881 (calcd for C27H36Br2O4Na, 605.0878).

Bromophycolide U (4): white, amorphous solid (0.95 mg, 0.0049% dry mass); [R]23D +84 (c 0.063, MeOH); UV (MeOH) λmax (log ε) 260 (3.72) nm; IR (NaCl) νmax 3352, 2926, 1715, 1605, 1456, 1273, 1111 cm-1; 1H NMR (CDCl3, 500 MHz) and 13C NMR (CDCl3, 125 MHz) data; 2D NMR data; HRESIMS [M+Na]+m/z 605.0871 (calcd for C27H36Br2O4Na, 605.0878).

Pharmacological Assays.

The pharmacological assays were run as in our previous reports. Kubanek et al., *Org. Lett.* 2005, 23, 5261-5264; Kubanek et al., *J. Nat. Prod.* 2006, 69, 731-735; Lane et al., *J. Org. Chem.* 2007, 72, 7343-7351; Lane et al., *J. Org. Chem.* 2009, 74, 2736-2742; Lane et al., *J. Proc. Natl. Acad. Sci. U.S.A.* 2009, 106, 7314-7319. Antimalarial activity was determined with a SYBR Green-based parasite proliferation assay. Antibacterial assays were performed using methicillin-resistant *Staphylococcus aureus* (MRSA, ATCC 33591) and vancomycin-resistant *Enterococcus faecium* (VREF, ATCC 700221) as test pathogens. Antifungal assays were performed using amphotericin B-resistant *Candida albicans* (ATCC 90873). Antitubercular activity was assessed against *Mycobacterium tuberculosis* strain H37Rv (ATCC 27294) using the microplate alamar blue assay (MABA).10 Anticancer assays were conducted using 12 human cancer cell lines including breast (BT-549, DU4475, MDAMD-468, and MDA-MB-231), colon (HCT-116), lung (SHP-77 and A549), prostate (PC-3, LNCaP-FGC, and DU145), ovarian (A2780/DDP-S), and leukemia (CCRF-CEM) cancer cell lines. In vitro cytotoxicity was tested by using MTS methods described previously. Lee et al., *Clin. Cancer Res.* 2001, 7, 1429-1437.

EXAMPLE 3

Antimalarial Meroditerpenes

Three antimalarial meroditerpenes have been isolated from two Fijian red macroalgae. The absolute stereochemistry of callophycolide A (compound I below), a unique macrolide from *Callophycus serratus*, was determined using a combination of Mosher's ester analysis, circular dichroism analysis with a dimolybdenum tetraacetate complex, and conformational analysis using NOEs.

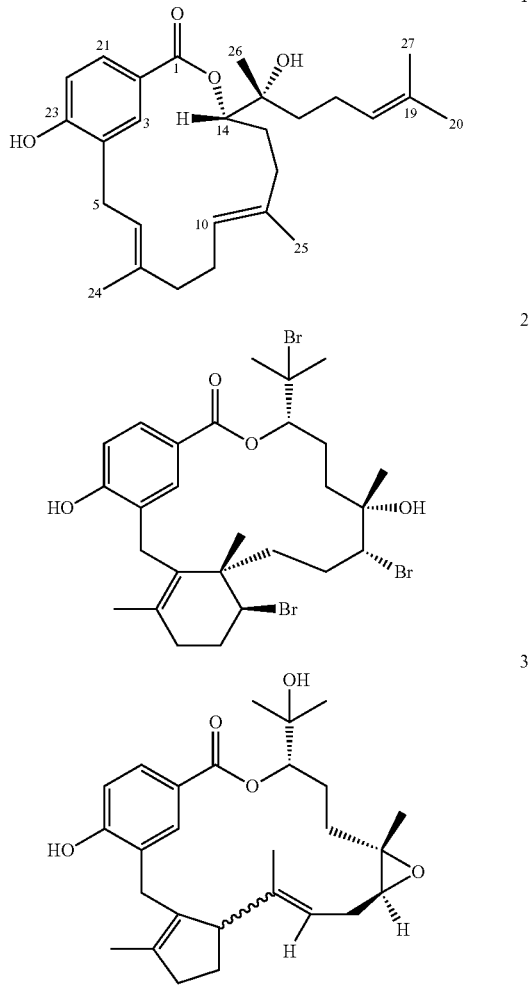

Continued efforts to uncover antimalarial natural products from understudied tropical red macroalgae led to the exploration of potent activity from two red algae, leading to the identification of an unusual non-brominated macrolide named callophycolide A (1).

*C. serratus* (family Solieriaceae, order Gigartinales, class Rhodophyceae, phylum Rhodophyta) was collected at depths of 2-3 m from Yanuca in the Fiji Islands (18° 23'57" S, 177° 57'59" E). Frozen *C. serratus* was extracted with MeOH and MeOH/DCM (1:1, 1:2) and subjected to liquid partitioning between MeOH/H$_2$O (9:1) and petroleum ether. The MeOH/H$_2$O ratio of the aqueous fraction was then adjusted to 3:2 and partitioned against chloroform. The chloroform-soluble fraction was then separated with multiple rounds of reversed-phase C$_{18}$ HPLC (Alltech Alltima C$_{18}$, 5 μm, 10×250 mm) with a gradient of MeCN (aq) to yield 1 from *C. serratus*.

Unlike previously isolated bromophycolides, callophycolide A (1) did not display a characteristic brominated isotopic pattern with HRESIMS, but showed an [M+H]$^+$ m/z of 427.2825, appropriate for a formula of C$_{27}$H$_{38}$O$_4$. The p-hydroxybenzoate segment common to all reported *C. serratus* secondary metabolites remained intact, apparent from the $^{13}$C and $^1$H NMR chemical shifts for positions 3 ($\delta_C$ 131.1; $\delta_H$ 7.85), 21 ($\delta_C$ 129.6; $\delta_H$ 7.73), 22 ($\delta_C$ 114.8; $\delta_H$ 6.78), and 23 ($\delta^C$ 158.0; OH $\delta_H$ 5.83). HMBC correlations from H$_2$-5 (δ 3.17, 3.49) to C-3, C-4 (δ 127.7), and C-23 connected the C-5 methylene to the p-hydroxybenzoate fragment, as in bromophycolides, but surprisingly C-5 was not connected to a substituted cyclohexene. Instead, a linear isoprene unit was established through COSY correlations between both H$_2$-5 protons and H-6 (δ 5.45), as well as HMBC correlations from Me-24 (δ 1.60) to C-6 (δ 122.7), C-7 (δ 136.8), and C-8 (δ 39.3). COSY correlations failed to establish the vicinal relationship of H$_2$-8 (δ 2.17, 2.27) and H$_2$-9 (δ 2.15, 2.23) due to substantial chemical shift overlap; instead, HSQC-TOCSY correlations were used to connect well-resolved carbons at C-8 and C-9 (δ 23.8). COSY correlations between both H$_2$-9 protons and H-10 (δ 5.19) and HMBC correlations from Me-25 (δ 1.59) to C-10 (δ 123.5), C-11 (δ 135.2), and C-12 (δ 35.8) connected a second isoprene unit within 1. HMBC correlations from H-14 (δ 4.75) to C-1 (δ 169.2), C-12 (δ 35.8), C-13 (δ 29.2), C-15 (δ 74.8), and Me-26 (δ$_C$ 22.0) provided strong evidence in support of a macrocyclic lactone framework and accounted for a third isoprene fragment. Me-26 (δ$_H$ 1.16) showed strong HMBC signals to C-14 (δ 82.1), C-15, and C-16 (δ 40.0), while vicinal COSY correlations established a C-16-C-17-C-18 connectivity. Allylic coupling was observed with weak COSY correlations between H-18 (δ 5.10) and both Me-20 (δ 1.66) and Me-27 (δ 1.60), establishing the diterpene head. This structural feature was further confirmed by HMBC correlations from both Me-20 and Me-27 to C-18 (δ 124.3), C-19 (δ 131.8), and to each other, completing the planar connectivity of 1.

ROESY data were used to assign the configurations of the olefins within the macrocyclic ring. NOEs observed between H-6 and both H$_2$-8 protons and between H$_b$-5 (δ 3.49) and Me-24 (δ 1.60) supported an E configuration for Δ. Similarly, ROESY correlations between H-10 (δ 5.19) and H$_a$-12 (δ 1.87) as well as between H$_b$-9 (δ 2.23) and Me-25 (δ 1.59) suggested an E configuration for Δ.

Absolute configuration at C-14 was determined by analysis of Mosher ester data derived from the methylated hydrolysis product 7. Hydrolyzed product 7 was acylated with each of R-(−)- and S-(+)-α-methoxy-α-(trifluoromethyl)phenylacetyl chloride (MTPA-Cl) to produce the corresponding S- and R-MTPA esters 7a and 7b, respectively. Analysis of the 1H NMR and HSQC-TOCSY spectra obtained for both esters permitted the assignment of the proton chemical shifts in proximity of the esterified carbon. Calculation of the Δδ$_{S-R}$ values established the absolute configuration of C-14 as S based upon empirical rules proposed by Ohtani et al. (J Am Chem Soc 1991, 113:4092).

Solution of the configuration at C-15 proved to be challenging relative to other stereocenters in 1. Frelek et al. reported a circular dichroism (CD) spectroscopic method for determining the absolute configuration of restricted and flexible vicinal diols complexed with dimolybdenum tetraacetate. After ligation to Mo$_2$, freerotation about flexible diols is substantially reduced due to steric requirements of the transition metal complex. The energetically preferred conformation of a flexible diol ligated to Mo$_2$ in a bidentate fashion is an antiperiplanar orientation of the O—C—C—R groups, with the bulky R-groups pointing away from the Mo$_2$ complex and the vicinal diols in a gauche conformation. The CD spectrum of the in situ formed Mo$_2$ complex with 7 showed a negative Cotton effect at 310 nm, which corresponded to a negative O—C—C—O dihedral angle as predicted by the helicity rule proposed by Frelek et al. (Curr Org Chem 2003, 7:1081). Molecular modeling was performed with HyperChem using the molecular mechanics MM+ force field method and conjugate gradient Polak Ribiere algorithm with RMS gradient of 0.001 kcal/A mol as described in Gorecki et al. (J Org Chem 2007, 72:2906). Molecular modeling of a 14S, 15S configuration in accordance with the lowest energy conformation predicted a positive O—C—C—O dihedral angle, ruling out this diastereomer and suggesting a 14S, 15R configuration, whose preferred conformation of the dimolybdenum complex could have yielded either a positive or negative torsional angle. A stable conformation of 1 could involve intramolecular hydrogen bonding between the C-15 hydroxy and C-1 carbonyl, as predicted by molecular modeling. This places the C-15 hydroxy anti to H-14 which is supported by NOEs observed between H-14 and both H$_b$-16 (δ 1.52) and Me-26; however this conformation is feasible for both 15R and 15S. An NOE correlation from H$_b$-16 to H$_b$-13 (δ 2.03) could differentiate between a 15R or 15S configuration, and inspection of 1D NOE spectra (irradiating H$_b$-16, acquired at −10° C.) showed the presence of this correlation. Lack of NOEs between H$_2$-13 protons and Me-26 implied an anti conformation of these groups and further supported a 15R stereochemical assignment. Overall, the combination of Mosher's ester analysis, CD analysis with a dimolybdenum tetraacetate complex, and conformational analysis using NOEs argue strongly for an absolute stereochemistry of 14S, 15R for 1.

Previously reported bromophycolides (e.g., bromophycolide A, 2) and related non-macrocyclic callophycoic acids and callophycols (Lane et al., J Org Chem 2007, 72:7343) exhibit antimalarial IC$_{50}$ values ranging from 0.3 to >100 μM, providing a detailed structure-activity relationship (SAR) analysis for this class of compounds. Lin et al., J Nat Prod 2010, 73:275. The identification of 1 provides additional insight into the SAR for 33 known C. serratus metabolites, in that 1 retains moderate antimalarial activity (IC$_{50}$=5.2 μM, Table 4) despite the complete absence of bromine atoms, similar to debromophycolide A, whose antimalarial IC$_{50}$ is >100 μM.

TABLE 4

Pharmacological Activity of 1-3

| Compd | Antimalarial activity IC$_{50}$ (μM) | Anticancer activity IC$_{50}$$^a$ (μM) | Antimicrobial MIC (μM) | | | |
|---|---|---|---|---|---|---|
| | | | MRSA$^b$ | VREF$^c$ | M. tuberculosis | ARCA$^d$ |
| 1 | 5.2 | 18 | 9.1 | 9.1 | 12 | >250 |
| 2 | 0.7 | 6.7 | 5.9 | 5.9 | 11 | 49 |
| 3 | >100 | >76 | NT | NT | >100 | >500 |

NT indicates not tested due to insufficient material.
$^a$Median of 12 cell lines.
$^b$Methicillin-resistant *Staphylococcus aureus*.
$^c$Vancomycin-resistant *Enterococcus faecium*.
$^d$Amphotericin B-resistant *Candida albicans*.

Furthermore, 1 has a carbon skeleton different from other bromophycolides, although its skeleton is not unprecedented and is shared with tocopherols Shin et al., J Chromatogr, A1994, 678:49. The lactonization pattern through C-14 in 1 is unique, and the absence of a substituted cyclohexene ring (compared to 2, $IC_{50}=0.7$ µM) suggests that this ring is not essential but can enhance antimalarial activity. Callophycolide A (1) was tested against 12 human cancer cell lines, exhibiting only modest cytotoxicity against most cell lines ($IC_{50}$ values ranging from 16 to 22 µM); the two most sensitive cell lines, CCRF-CEM (leukemia tumor cells) and SHP-77 (lung tumor cells), showed moderate $IC_{50}$ values of 7.5 and 9.2 µM, respectively. Callophycolide A (1) inhibited bacterial growth in the low micromolar range but was ineffective at deterring growth of human pathogenic fungi (Table 4).

Compound I is an unusual scaffold when compared to current natural antimalarial treatments, such as the quinines and artemisinins. Meroditerpene macroalgal compounds are therefore potentially useful as novel templates for antimalarial drugs.

Compound data.

Callophycolide A (1): pale yellow oil (4.0 mg, 0.021% dry mass); $[\alpha]^{24}_D$ +200 (c 0.01, MeOH); UV (MeOH) $\kappa_{max}$ (log ε) 260 (4.06) nm; $^1H$, $^{13}C$, NOE, COSY, HSQC-TOCSY, and HMBC NMR data; HRESIMS [M+H]+m/z 427.2825 (calcd for $C_{27}H_{39}O_4$, 427.2842) and [M+Na] m/z 449.2623 (calcd for $C_{27}H_{38}O_4Na$, 449.2668).

EXAMPLE 5

Synthetic Derivatives and Structure-Activity Testing

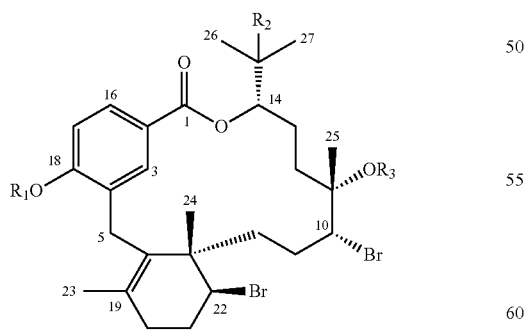

1 $R_1$ = H, $R_2$ = Br, $R_3$ = H
2 $R_1$ = H, $R_2$ = OH, $R_3$ = H
7 $R_1$ = Ac, $R_2$ = Br, $R_3$ = H
8 $R_1$ = Me, $R_2$ = Br, $R_3$ = H
9 $R_1$ = Me, $R_2$ = Br, $R_3$ = Me

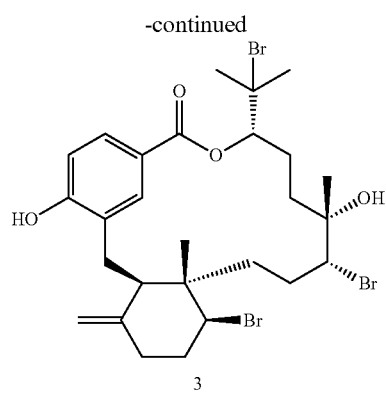

3

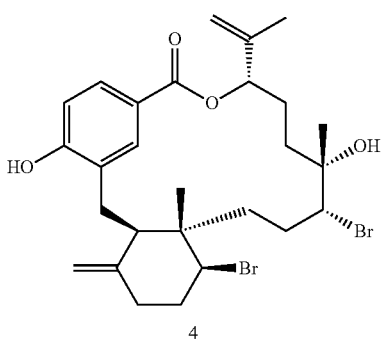

4

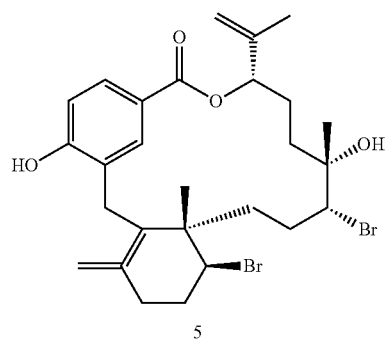

5

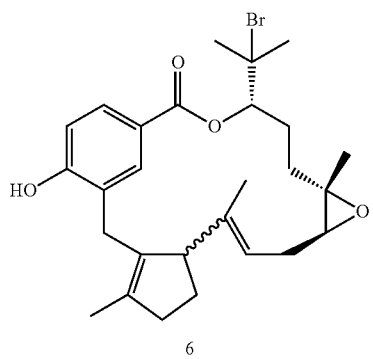

6

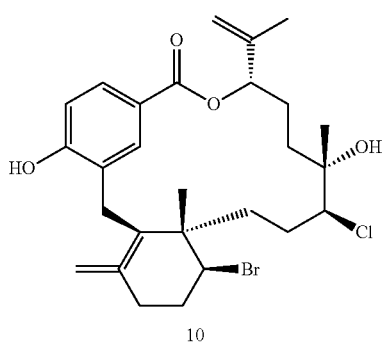

10

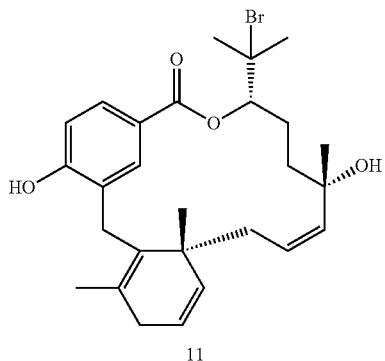

11

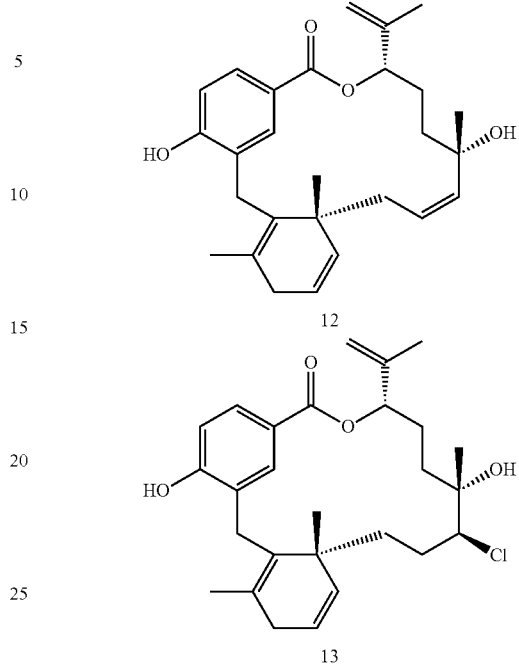

12

13

Thirty-three unique *C. serratus* natural products have been isolated, with $IC_{50}$ values ranged from 0.3 to >100 μM, providing a small library to analyze SAR trends (representative natural products 1-6). Several semi-synthetic derivatives of 1 were also prepared (7-13) to further enhance SAR studies and to provide insights for potential future designs of bromophycolide-inspired synthetic compounds.

When examining the natural product SAR trends, the most striking observation was related to the diterpene head. While replacing the bromine at C15 with an isoprene functionality caused little change in antimalarial activity, substitution of a hydroxyl group at C15 resulted in dramatic loss of activity (Scheme 1), suggesting that a hydrogen bond donating group is poorly suited in this position.

Scheme 1. Structure-activity relationship summary of *C. serratus* natural products and bromophycolide A (1) semi-synthetic derivatives.

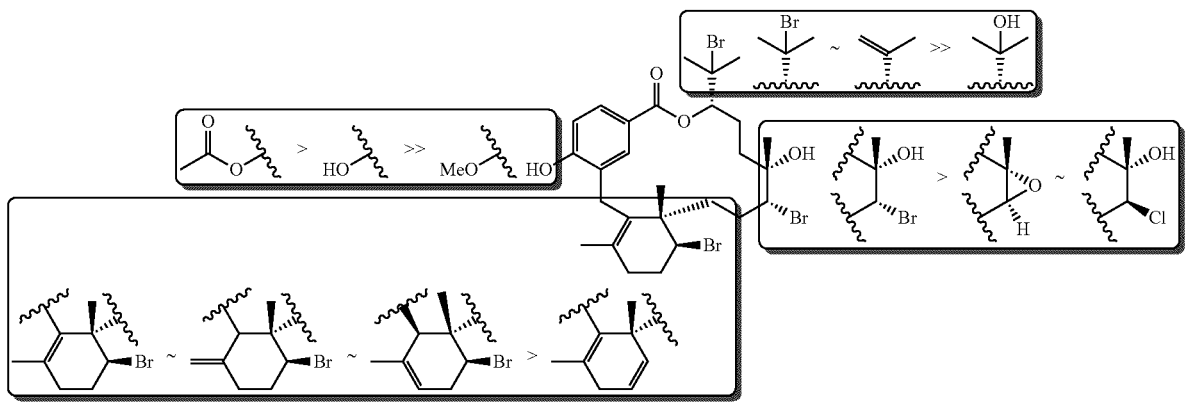

Greater potency is indicated by ">", lesser potency by "<", similar potency by "~".

Moving to functional groups in the aliphatic macrocycle, synthetic modifications at C10 and C11 also did not significantly affect activity, and replacing the bromine at C10 with chlorine resulted in a slight decrease in activity, although it should be noted that the configuration at C10 was inverted (4 vs. 10). Regioisomerization of the double bond in the cyclohexene ring in both natural products and synthetic derivatives also demonstrated only minor alterations in activity. Interestingly, elimination of all bromines from 1 only moderately decreased the $IC_{50}$ value from 0.65 to 3.5 µM (1 vs. 12) whereas the natural product 6 was completely inactive. The final portion of 1 to investigate was the p-hydroxybenzoate group. Acylation of the phenol in 1 to 7 resulted in a slight increase in activity. Surprisingly, methylation of the phenol in 1 to 8 led to a 30-fold decrease in activity. Collectively, these data suggest that positions C15 and C18 have the most striking effects on antimalarial activity.

TABLE 5

Antimalarial activities of bromophycolides A (1), C (2), D (3), E (4), M (5), debromophycolide A (6), and semi-synthetic derivatives of bromophycolide A (7-13).

| cmpd | P. falciparum (3D7) $IC_{50}$ (µM) |
|---|---|
| 1 | 0.66 |
| 2 | 56 |
| 3 | 0.35 |
| 4 | 0.82 |
| 5 | 0.55 |
| 6 | >100 |
| 7 | 0.24 |
| 8 | 23 |
| 9 | 21 |
| 10 | 3.1 |
| 11 | 4.6 |
| 12 | 3.5 |
| 13 | 2.7 |

The foregoing is illustrative of the present invention, and is not to be construed as limiting thereof. The invention is defined by the following claims, with equivalents of the claims to be included therein.

That which is claimed is:

1. A method of treating malaria in a subject in need thereof, comprising administering to said subject in a treatment effective amount a composition comprising a compound selected from the group consisting of:

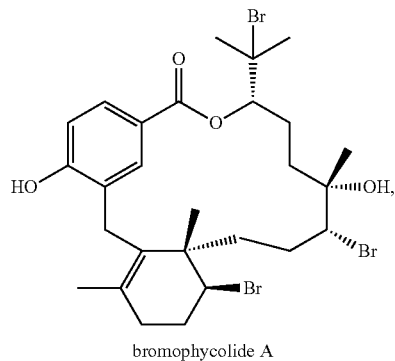

bromophycolide A

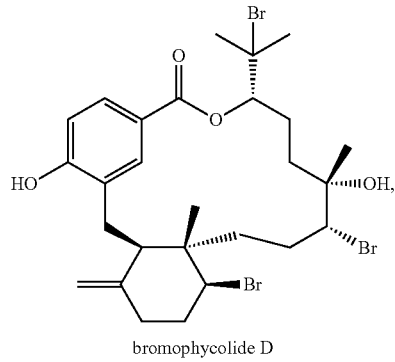

bromophycolide D

TABLE 6

Efficacies of bromophycolide A (1), 18-OAc-bromophycolide A (7) and amodiaquine (AMQ) against three *Plasmodium falciparum* strains, in inhibition of heme crystallization, and cytotoxicity against healthy human cells.

| Cmpd | 3D7 $IC_{50}$ (nM)[a] | Dd2 $IC_{50}$ (nM)[b] | HB3 $IC_{50}$ (nM)[a] | $IC_{50}$ for heme crystallization (equivalents)[c] | Cytotoxicity ($IC_{50}$ µM) | | |
|---|---|---|---|---|---|---|---|
| | | | | | Vero | J774 | HepG2 |
| 1 | 658 | 497 | 565 | 2.5 ± 0.13 | 34.6 | 19.0 | 21.3 |
| 7 | 241 | 304 | 431 | 2.0 ± 0.15 | 74.0 | 24.7 | 38.5 |
| AMQ | 7.8[d] | — | 8.5[d] | 1.2 ± 0.19 | — | — | — |

[a]3D7 and HB3 = chloroquine-sensitive parasites

[b]Dd2 = chloroquine-resistant parasite

[c]$IC_{50}$ values in Ncokazi & Egan (Anal Biochem 2005, 338: 306) were reported as molar equivalents of drug to heme

[d]From Hawley et al. (Antimicrob Agents Chemother 1998, 42: 682)

-continued
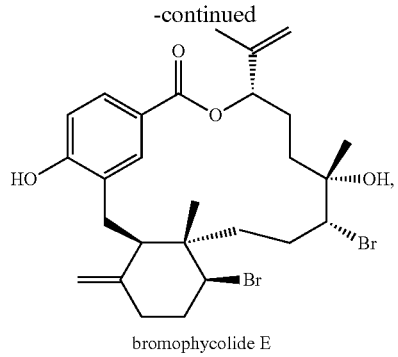
bromophycolide E
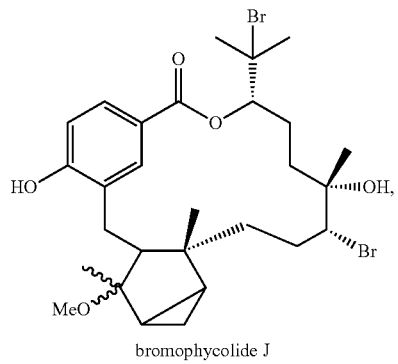
bromophycolide J
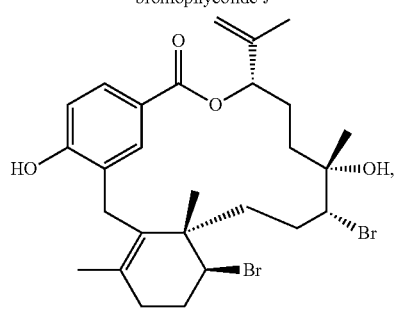
bromophycolide M
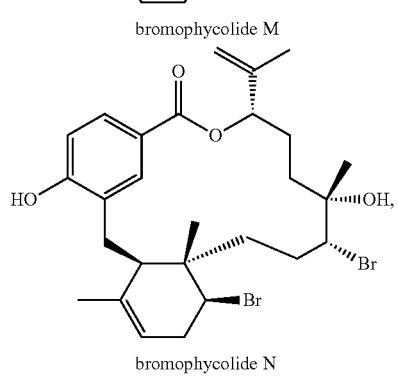
bromophycolide N
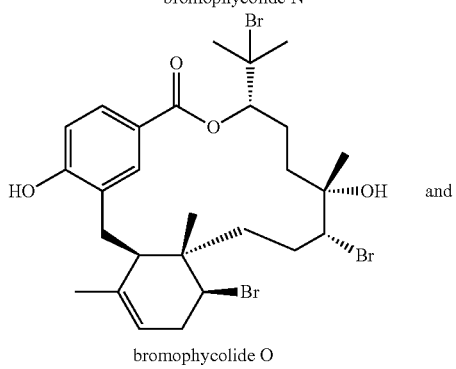
bromophycolide O
-continued
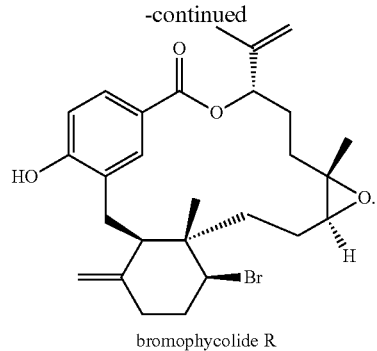
bromophycolide R
2. The method of claim 1, wherein said compound is selected from the group consisting of:
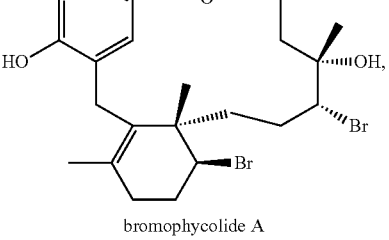
bromophycolide A
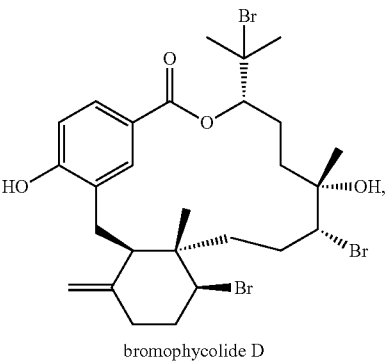
bromophycolide D
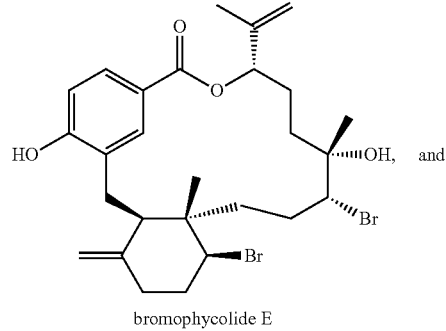
bromophycolide E

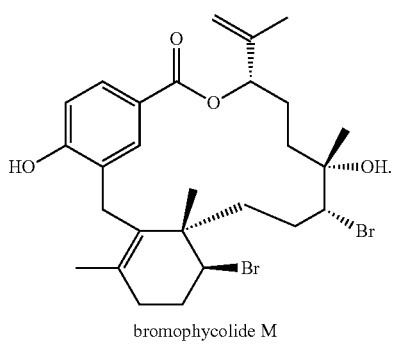

bromophycolide M

3. A method of treating malaria in a subject in need thereof, comprising administering to said subject in a treatment effective amount a composition comprising a compound:

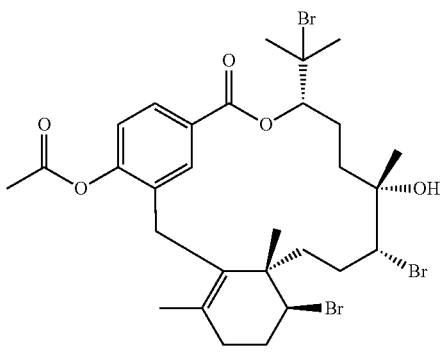

bromophycolide A acetyl derivative or a pharmaceutically acceptable salt thereof,
in a pharmaceutically acceptable carrier.

4. The method of claim 1, wherein said composition is formulated for oral, rectal, or parenteral administration.

5. The method of claim 1, wherein said composition further comprises another anti-malaria agent selected from the group consisting of: quinine, chloroquine, artemisinin, and an artemisinin derivative.

6. The method of claim 1, wherein said compound is:

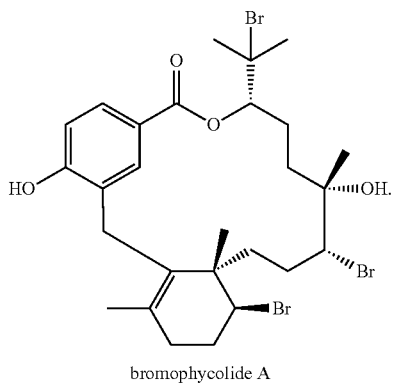 [SMILES: CC1=C2Cc3cc(ccc3O)C(=O)O[C@H](C(C)(C)Br)CC[C@](C)(O)[C@H](Br)CC[C@]2(C)[C@@H](Br)CC1]

bromophycolide A

7. A method of treating malaria in a subject in need thereof, comprising administering to said subject in a treatment effective amount a composition comprising a compound selected from the group consisting of:

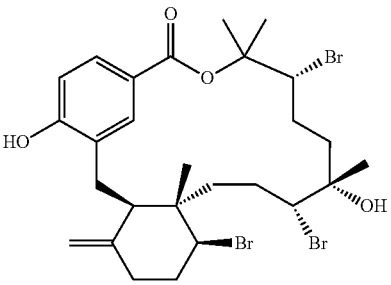

bromophycolide H and

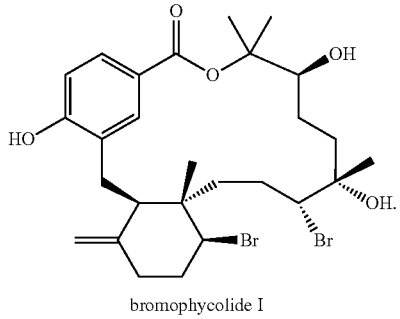

bromophycolide I

8. A method of treating malaria in a subject in need thereof, comprising administering to said subject in a treatment effective amount a composition comprising a compound:

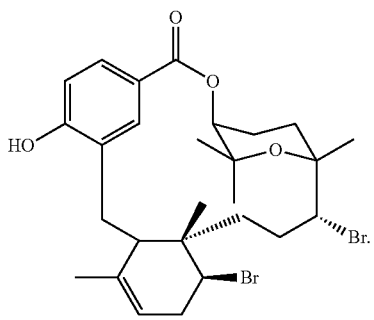

bromophycolide Q

9. The method of claim 7, wherein said composition is formulated for oral, rectal, or parenteral administration.

10. The method of claim 7, wherein said composition further comprises another anti-malaria agent selected from the group consisting of: quinine, chloroquine, artemisinin, and an artemisinin derivative.

11. The method of claim 8, wherein said composition is formulated for oral, rectal, or parenteral administration.

12. The method of claim 8, wherein said composition further comprises another anti-malaria agent selected from the group consisting of: quinine, chloroquine, artemisinin, and an artemisinin derivative.

* * * * *

UNITED STATES PATENT AND TRADEMARK OFFICE
CERTIFICATE OF CORRECTION

PATENT NO. : 8,481,757 B2
APPLICATION NO. : 13/021171
DATED : July 9, 2013
INVENTOR(S) : Kubanek et al.

Page 1 of 1

It is certified that error appears in the above-identified patent and that said Letters Patent is hereby corrected as shown below:

On Title Page:
Item 73, Assignees:
Please correct "Georgua Tech Research Corporation, Atlanta, GA (US);"
    to read -- Georgia Tech Research Corporation, Atlanta, GA (US); --

In the Specification:
Column 28, Line 5: Please correct "concentration of 50"
    to read -- concentration of 50 µM. --

Column 41, Lines 1-18, Item 10: Please correct the compound below:

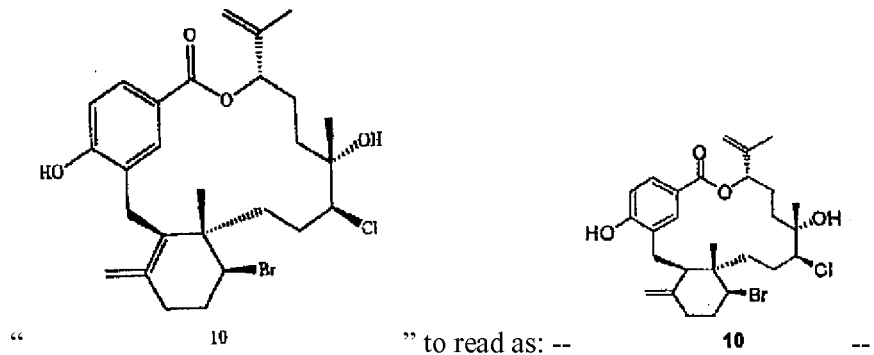

Signed and Sealed this
Twenty-third Day of September, 2014

Michelle K. Lee
*Deputy Director of the United States Patent and Trademark Office*